United States Patent [19]
Green et al.

[11] Patent Number: 5,558,266
[45] Date of Patent: Sep. 24, 1996

[54] APPARATUS FOR APPLYING SURGICAL FASTENERS

[75] Inventors: David T. Green, Westport; Henry Bolanos, East Norwalk; Keith Ratcliff, Sandy Hook; Lisa W. Heaton, Norwalk; John C. Robertson, Bloomfield, all of Conn.

[73] Assignee: United States Surgical Corporation, Norwalk, Conn.

[21] Appl. No.: 234,712

[22] Filed: Apr. 28, 1994

Related U.S. Application Data

[63] Continuation of Ser. No. 779,505, Oct. 18, 1991, abandoned.

[51] Int. Cl.$^6$ .................................................. A61B 17/072
[52] U.S. Cl. ...................... 227/178.1; 227/19; 227/175.1
[58] Field of Search .......................... 227/19, 175, 176, 227/177, 178, 180, 181, 175.1, 175.2, 175.3, 175.4, 176.1, 177.1, 178.1, 180.1, 181.1

[56] References Cited

U.S. PATENT DOCUMENTS

| | | | |
|---|---|---|---|
| 804,229 | 11/1905 | Hutchinson . | |
| 2,891,250 | 6/1959 | Hirata . | |
| 3,079,608 | 3/1963 | Pabkin | 227/19 X |
| 3,080,564 | 3/1963 | Strekopitov et al. . | |
| 3,252,643 | 5/1966 | Strekopytov et al. . | |
| 3,269,630 | 8/1966 | Fleischer . | |
| 3,593,903 | 7/1971 | Astafiev et al. | 227/19 X |
| 3,692,224 | 9/1972 | Astafiev et al. | 227/19 |
| 3,795,034 | 3/1974 | Strekopytov et al. . | |
| 4,349,028 | 9/1982 | Green . | |
| 4,354,628 | 10/1982 | Green | 227/19 |
| 4,442,964 | 4/1984 | Becht | 227/8 |
| 4,470,533 | 9/1984 | Schuler | 227/19 |
| 4,506,670 | 3/1985 | Crossley | 227/19 X |
| 4,508,253 | 4/1985 | Green | 227/19 |
| 4,513,746 | 4/1985 | Aranyi et al. | 227/19 X |
| 4,522,327 | 6/1985 | Korthoff et al. . | |
| 4,527,724 | 7/1985 | Chow et al. | 227/8 |
| 4,530,453 | 7/1985 | Green | 227/19 |
| 4,566,620 | 1/1986 | Green et al. | 227/19 |
| 4,573,622 | 3/1986 | Green et al. | 227/19 |
| 4,580,712 | 4/1986 | Green | 227/19 |
| 4,585,153 | 4/1986 | Failla et al. | 227/19 |
| 4,591,085 | 5/1986 | Di Giovanni | 227/8 |
| 4,605,004 | 8/1986 | Di Giovanni et al. . | |
| 4,606,344 | 8/1986 | Di Giovanni . | |
| 4,606,345 | 8/1986 | Dorband et al. . | |
| 4,607,636 | 8/1986 | Kula et al. . | |
| 4,632,290 | 12/1986 | Green et al. | 227/19 |
| 4,715,520 | 12/1987 | Roehr, Jr. et al. | 227/19 |
| 4,728,020 | 3/1988 | Green et al. | 227/19 |
| 4,788,978 | 12/1988 | Strekopytov et al. . | |
| 4,848,637 | 7/1989 | Pruitt | 227/19 |
| 4,869,414 | 9/1989 | Green et al. | 227/19 |
| 4,930,503 | 6/1990 | Pruitt | 227/178 |
| 4,938,408 | 7/1990 | Bedi et al. | 227/19 X |
| 4,941,623 | 7/1990 | Pruitt | 227/19 |
| 4,964,559 | 10/1990 | Deniega et al. | 227/19 X |

(List continued on next page.)

FOREIGN PATENT DOCUMENTS

| | | |
|---|---|---|
| 0157888 | 3/1984 | European Pat. Off. . |
| 0136950 | 4/1985 | European Pat. Off. . |
| 0220029 | 4/1987 | European Pat. Off. . |
| 0273468 | 7/1988 | European Pat. Off. . |
| 2542188 | 3/1983 | France . |
| 1835500 | 4/1961 | Germany . |
| 119846 | 1/1959 | U.S.S.R. ............................. 227/178 |
| 1555455 | 11/1979 | United Kingdom . |
| 2141066 | 12/1984 | United Kingdom . |

*Primary Examiner*—Rinaldi I. Rada

[57] ABSTRACT

A surgical stapling or fastening instrument for applying surgical fasteners to tissue having an adjustable closure mechanism to linearly approximate the distance between the jaw members of the instrument. The adjustable closure mechanism consists of a retaining mechanism and a linkage structure which is actuable to linearly urge the jaw members towards each other. A coupling arrangement is also provided which permits firing of the staples or fasteners only when the jaw members are approximated a predetermined distance towards each other.

66 Claims, 16 Drawing Sheets

U.S. PATENT DOCUMENTS

| | | | |
|---|---|---|---|
| 4,978,049 | 12/1990 | Green | 227/178 |
| 4,994,065 | 2/1991 | Gibbs et al. | 606/92 |
| 5,018,657 | 5/1991 | Pedlick et al. | 227/19 X |
| 5,027,834 | 7/1991 | Pruitt . | |
| 5,040,715 | 8/1991 | Green et al. | 227/180 X |
| 5,100,042 | 3/1992 | Gravener et al. . | |
| 5,137,198 | 8/1992 | Nobis et al. . | |
| 5,190,203 | 3/1993 | Rodak . | |
| 5,240,163 | 8/1993 | Stein et al. . | |

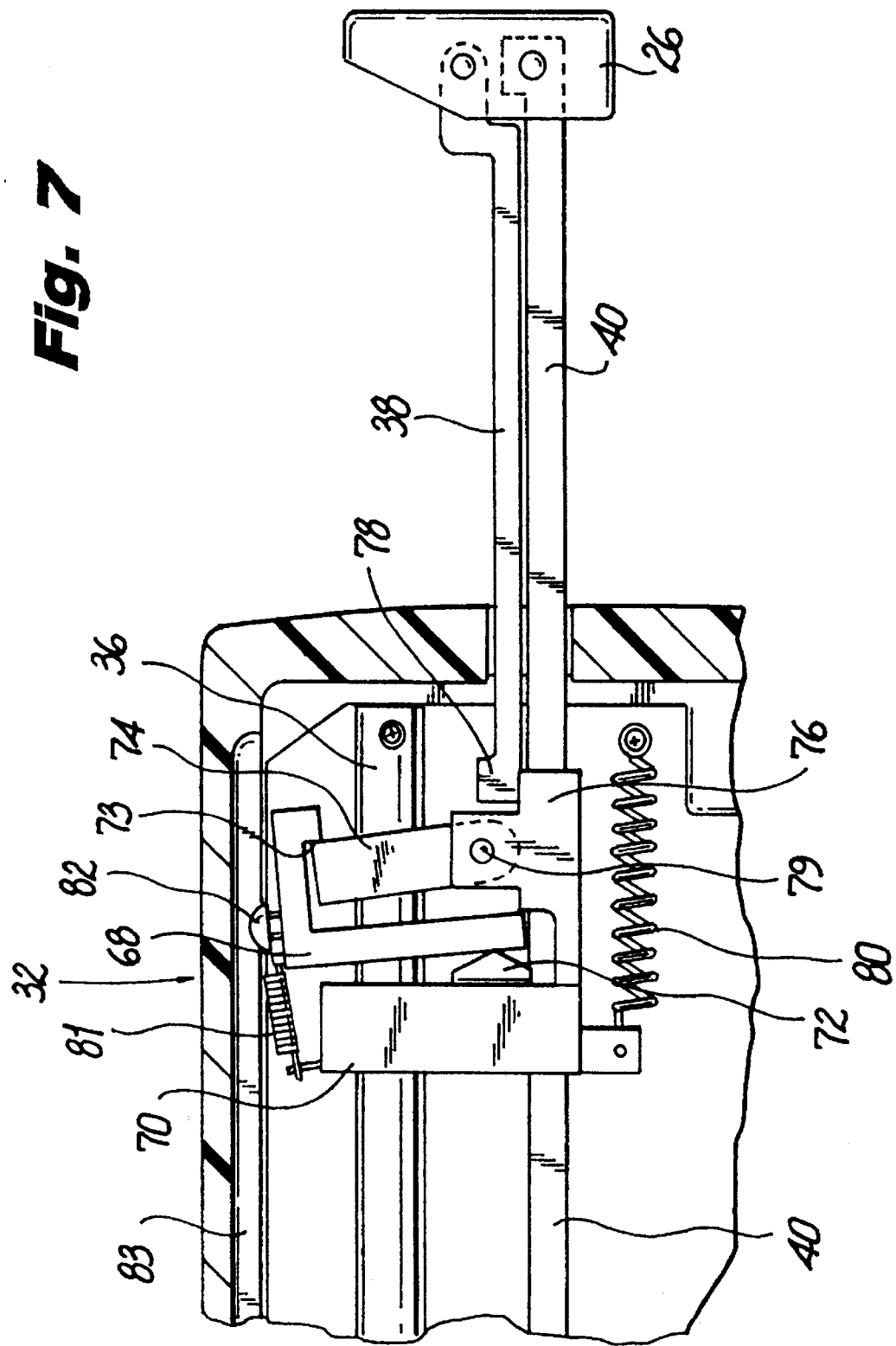

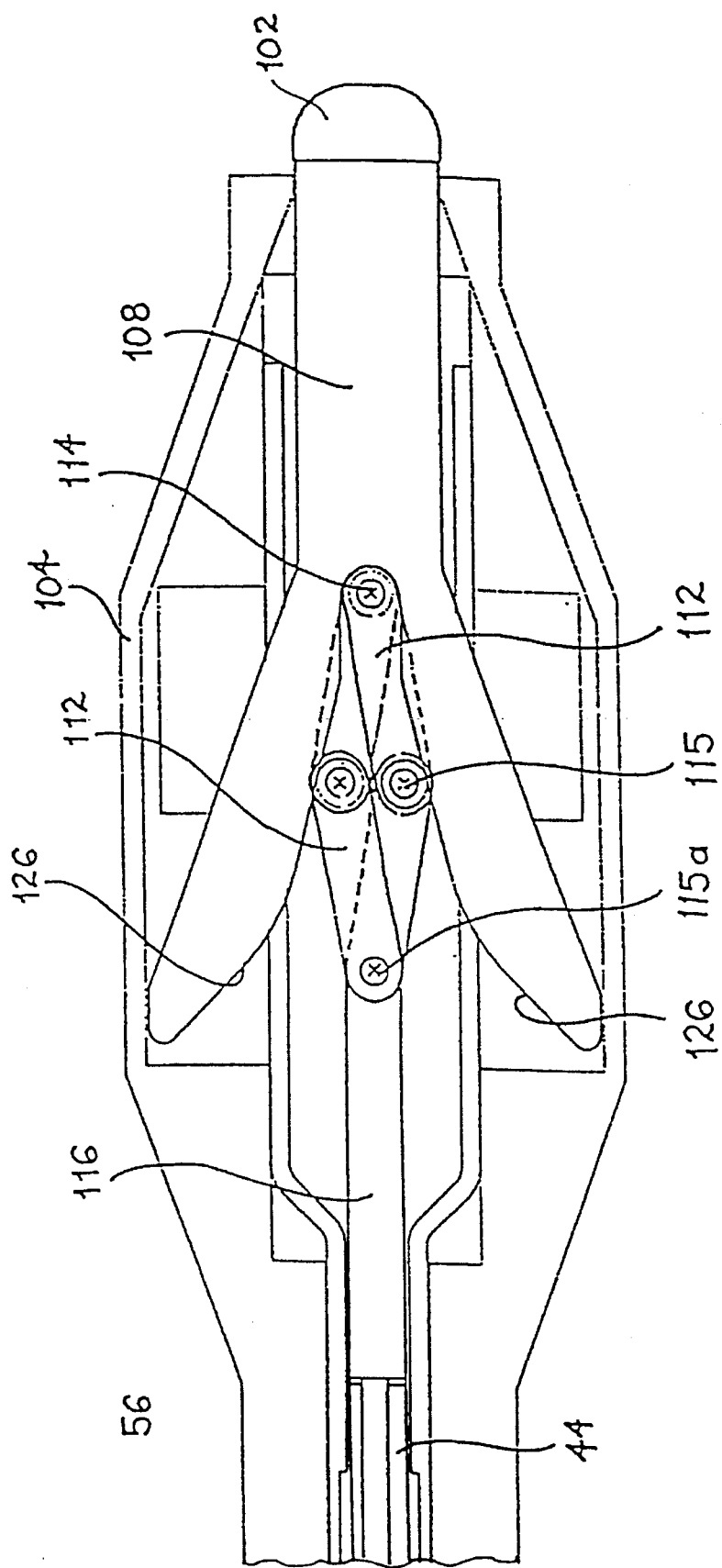

APPARATUS FOR APPLYING SURGICAL FASTENERS

This is a continuation of application Ser. No. 07/779,505 filed on Oct. 18, 1991, now abandoned.

BACKGROUND OF THE INVENTION

1. Field of the Invention

The present invention relates to surgical instruments for applying surgical fasteners or staples to body tissue, and more particularly to an apparatus for applying surgical fasteners having adjustable mechanisms for controlling the spacing between the jaw members through which the tissue passes during the fastening or stapling procedures.

2. Discussion of the Related Art

Surgical fastening devices having means for controlling the spacing between the jaw members are well known in the art. These devices typically include indicating means to provide a reading of the spacing between the jaw members. Devices are also known in the art which provide latching mechanisms to actuate the firing mechanism only when the distance between the jaws is within a preset range. These devices typically include a complex lock-out mechanism.

Various closing mechanisms are provided in the prior art for use with surgical fastening devices. The most notable of these devices utilize a complex worm gear-type arrangement or screw beating member to open and close the spacing between the jaw members of the surgical fastening apparatus. These devices generally provide a rotatable knob or wing-like assembly at the trigger end of the device remote from the jaw mechanism which carries the fastener cartridge, and a screw-like mechanism is provided that passes through the body of the device to translate the rotational movement of the knob into longitudinal movement of the cartridge frame to open and close the spacing between the jaws. As the jaw members are closed around a tissue site to which fasteners are to be applied, the surgeon must grasp the device with one hand while rotating the knob or wing-like assembly with the other hand. As the jaws members close about the tissue to pinch the tissue therebetween, the surgeon then ceases rotation and activates the trigger mechanism to drive the fasteners into the tissue. Several known devices provide a trigger-like mechanism, while others provide a secondary rotatable knob for driving the fasteners by rotational movement. Many devices provide an indicator means near the rotatable knob which gives a visual indication of the spacing between the jaw members prior to firing.

These prior art devices are subject to several disadvantages in both use and construction which render these devices difficult to operate and expensive to manufacture. Many of the devices are cumbersome in use in that the surgeon must operate the device with both hands, holding the body of the instrument in one hand while rotating the knob or wing assembly with the other hand. This may lead to inaccurate stapling or fastening since the surgeon is unable to guide the tissue to be stapled or fastened with his free hand while closing the jaws about the tissue. Furthermore, the number of interacting components provides inaccuracies due to normal break down of tolerances. In addition, the gear arrangement may become worn during extended use, thus rendering an imprecise grasping action at the jaws.

Furthermore, these prior art devices generally involve a complex construction in which a precisely machined or cast worm gear must be constructed and incorporated into the device. This of course increases the cost of manufacturing, and requires a sophisticated assembly procedure to properly locate the worm gear in the instrument to control the spacing between the jaws.

Typical devices having a rotatable knob at the end portion adjacent the handle mechanism of the surgical stapling or fastening device are disclosed in, among others, U.S. Pat. No. 4,930,503 to Pruitt, U.S. Pat. No. 4,788,978 to Strekopytov et al., and U.S. Pat. No. 4,606,344 to DiGiovanni. In each of these devices, an elongated rod member having screw threads machined thereon is provided, which connects a rotatable knob positioned adjacent the handle members to a pusher mechanism which urges a movable jaw in a forward direction toward a stationary jaw to close the spacing between the jaw members. When a desired spacing is reached, a trigger mechanism may be activated to fire the fasteners through the tissue into the anvil member mounted on the stationary jaw. To remove the fastening instrument after application of the fasteners, the knob is rotated in an opposite direction which turns the screw threaded rod member to move the movable jaw member away from the stationary jaw member so that the entire device maybe removed from the tissue.

Surgical fastening instruments having a wing like arrangement positioned adjacent the handle assembly of a device for moving a movable jaw toward a stationary jaws for affixing surgical fasteners to tissue are disclosed in U.S. Pat. No. 4,442,964 to Becht, U.S. Pat. No. 4,354,628 to Green, and U.S. Pat. No. 3,795,034 to Strekopytov et al. These devices are similar to those described above except for the provision of a rotatable wing member in place of the rotatable knob. These devices are also provided with a screw threaded rod member which, when rotated, urges a movable jaw towards a stationary jaw to close the jaw members around tissue to be fastened together. After the application of surgical fasteners, the wing assembly is rotated in an opposite direction to draw the movable jaw away from the stationary jaw so that the instrument maybe removed from the tissue.

Surgical stapling of fastening instruments having a pivotable mechanism external to the device for moving a movable jaw toward a stationary jaw prior to affixing surgical fasteners to tissue are disclosed in, among others, U.S. Pat. No. 3,269,630 to Fleischer, U.S. Pat. No. 4,530,453 to Green, U.S. Pat. No. 4,715,520 to Roehr, Jr. et al., and U.S. Pat. No. 4,978,049 to Green.

Green ('453), Roehr, Jr. et at. and Green ('049) each disclose a pivotable lever member which urges a movable jaw into proximity of a stationary jaw prior to application of the surgical fasteners. Fleischer discloses a surgical stapling instrument in which a pivotable handle urges the movable staple cartridge against the tissue in the direction of the stationary jaw and fires the staples in the same motion. In each of these devices, removal of the instrument after firing of the surgical fasteners is accomplished by pivoting the lever mechanism in the opposite direction to open the jaw members by moving the movable jaw away from the stationary jaw.

Pending U.S. patent application Ser. No. 593,697 filed Oct. 5, 1990, discloses a spring biased pivotal catch member for approximating the jaws which is held in selected position by a pointed lance member.

The novel surgical stapling or surgical fastening device of the present invention obviates the disadvantages encountered in the prior art and provides an efficient surgical fastening device having an adjustable closure mechanism for controlling the spacing between the jaw members of the surgical fastening apparatus. The device of the present invention allows a surgeon to operate a surgical fastener with one hand while freeing the other hand to assist in the surgical procedure. Furthermore, the present invention provides a novel means for coupling the fastener driving mechanism to the firing mechanism when the jaws are approximated to a preset distance. The device of the present invention is of lightweight construction and provides ease of handling through the provision of a thumb controlled adjustable closure mechanism which permits a surgeon to set the spacing between the jaw members and fire the device while using only one hand.

SUMMARY OF THE INVENTION

The present invention provides a surgical fastening device having a novel mechanism for adjusting the distance between the movable jaw and the stationary jaw prior to the application of fasteners to the body tissue. The adjustable mechanism controls the closing of the jaw mechanism to approximate the distance between the jaw members prior to activation of the trigger mechanism to fire the fasteners. The device of the present invention may be operated with one hand, which frees the surgeon to accurately locate the tissue to be repaired and to place the fasteners in the proper position during the procedure. The adjustable closure mechanism is operable by using the thumb of the hand which holds the device, and linearly moves the stapling mechanism to properly approximate the distance between the jaw members. The adjustable closure mechanism of the present invention eliminates many moving parts associated with prior devices, and provides a device which is lightweight, and easy to use by allowing the surgeon to set and release the device with one hand.

The adjustable closure mechanism of the present invention may be used with any surgical instrument having jaw members which include a stationary jaw and a movable jaw, or two movable jaws, in which the spacing between the jaw members is adjustable to accommodate various thicknesses of tissue to be secured. The provision of the push button at the handle end of the instrument and the elimination of numerous complex moving parts which are common in prior art devices allows the surgeon to approximate the distance between the jaw members in a fast and efficient manner to position the jaws in the proper alignment for the application of surgical fasteners.

The apparatus of the present invention comprises a first jaw member and a second jaw member in which the first jaw member includes a plurality of fasteners positioned in a cartridge which is movable with the first jaw member towards the stationary second jaw member. The second jaw member may include an anvil surface for clinching the fasteners, or may include means for engaging the fasteners to secured the tissue therebetween. Means for advancing the first jaw member towards the second jaw member to grip the tissue between the jaws are provided, as well as releasable means for retaining the advancing means along a linear path of travel to selectively position the first jaw member in relation to the second jaw member. Means for driving the fasteners into the tissue subsequent to positioning the jaws members in relation to each other by the advancement means is also provided, and the advancement means of the apparatus of the present invention is independent of the driving means.

In a preferred embodiment a push button mechanism is provided at the handle end of the device which may be linearly displaced by the thumb of the surgeon. As the push button and slider bar arrangement is urged forwardly towards the jaws, the releasable retaining means is also urged forwardly within the housing of the apparatus to selectively position the jaws members in relation to each other. As the slider bar and releasable retaining means are continuously moved forward, a linkage arrangement is activated which urges the cartridge frame forward so that the cartridge moves towards the anvil. When the linkage arrangement is fully actuated, the proper distance between the jaw members is set, so that the trigger mechanism may be actuated to drive the fasteners through the tissues.

Preferably, a coupling mechanism is provided which couples the fastener driving means to the trigger mechanism to allow for driving of the staples or fasteners when the proper distance between the jaw members is set. As the slider mechanism is moved forward and the linkage arrangement actuated, the fastener driving means is urged forwardly with the cartridge frame. A coupling arm, which is connected at one end to the trigger mechanism, slides along a beating surface on the driving means until the slider mechanism is fully deployed. At this point, a camming edge of the coupling arm engages a notch in the beating surface of the driving means to couple the trigger mechanism to the driving means. At this point, the proper distance between the jaw members is set and the fastener means may be driven into the tissue.

After the fastening means have been driven into the tissue, the releasable retaining mechanism may be disengaged so that the jaw members may be returned to their original position whereby the fastening device may be removed from the surgical site. In the preferred embodiment, the push button is pivotable to move a second rod member which contacts a release lever which disengages the retaining means. In a second embodiment, a release knob is provided which extends through the housing of the fastening apparatus and which may be pivoted to release the retaining means.

BRIEF DESCRIPTION OF THE DRAWINGS

The foregoing features of the present invention will become more readily apparent and may be understood by referring to the following detailed description of an illustrative embodiment of the surgical fastening instrument and its novel adjustable closure mechanism, taken in conjunction with the accompanying drawings, in which:

FIG. 7 illustrates the retaining means of the present invention at the handle end of the device of FIG. 2 in the at rest condition;

FIG. 13 illustrates a top plan cutaway view of the device of FIG. 10 showing the linkage arrangement of the adjustable closure mechanism of the present invention in a fully deployed condition;

DETAILED DESCRIPTION OF THE PREFERRED EMBODIMENTS

Figure 1:
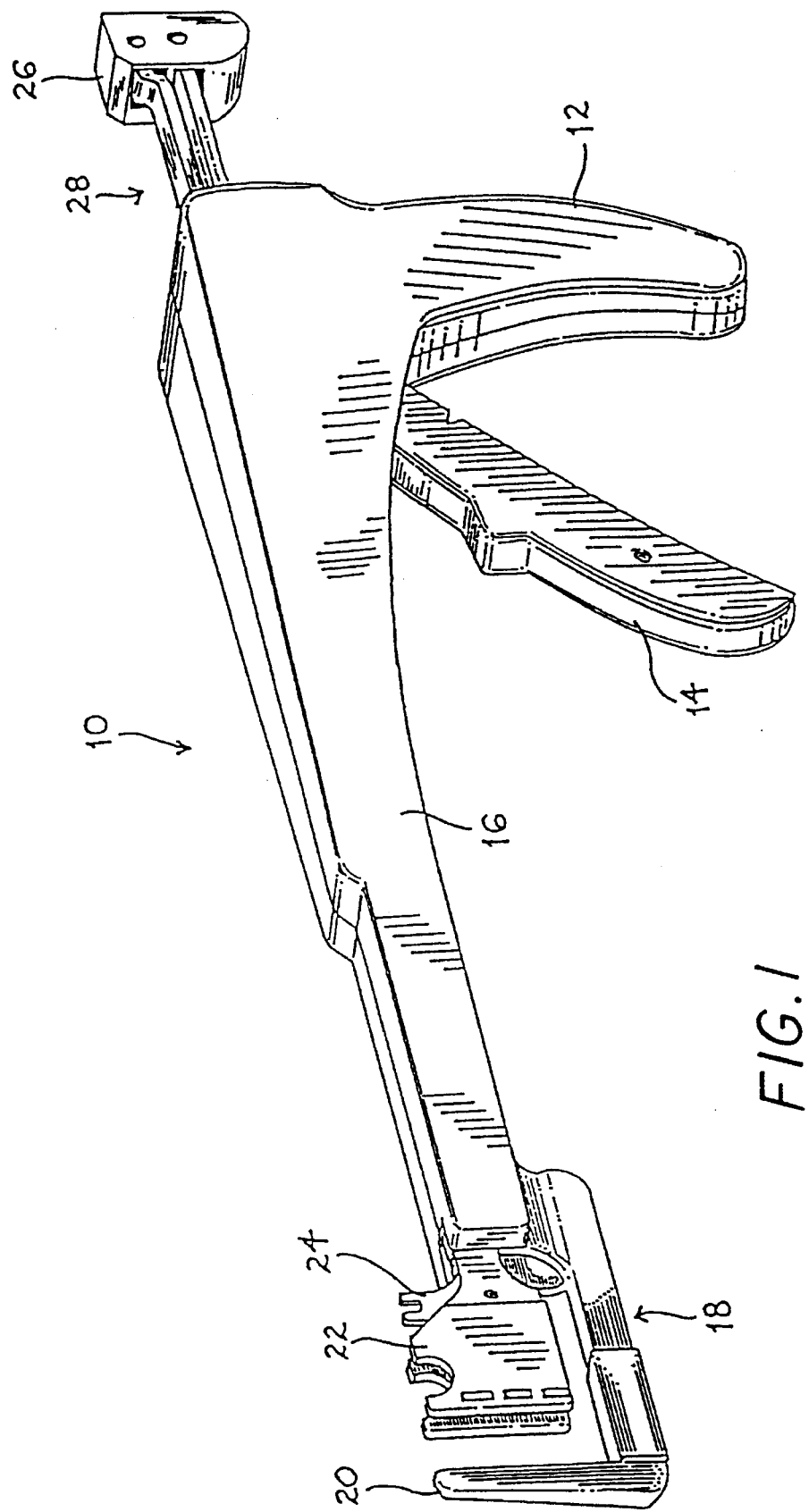
FIG. 1 illustrates a perspective view of a surgical fastening instrument employing the adjustable closure mechanism of the present invention.
Figure 10:
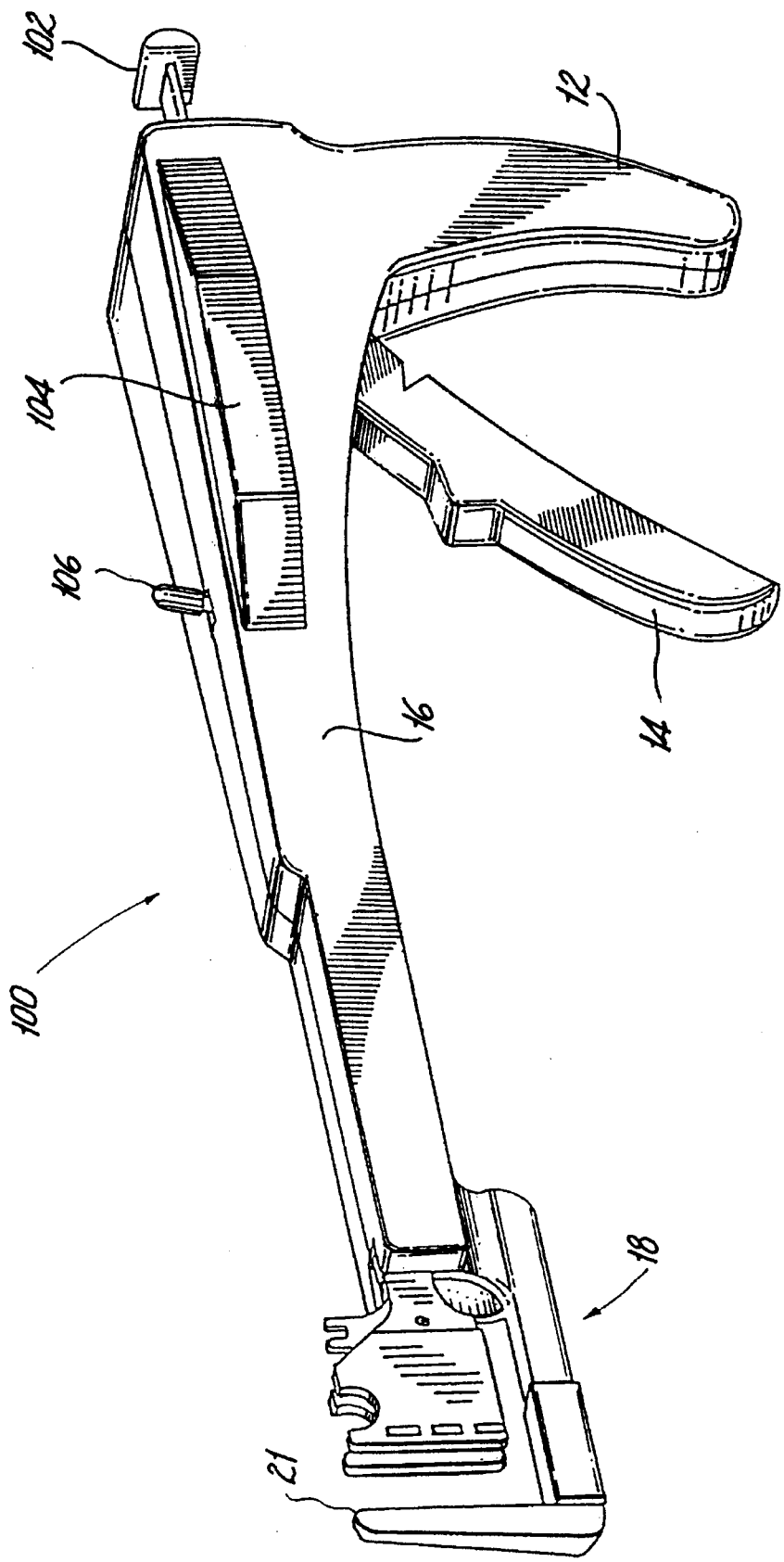
FIG. 10 illustrates a perspective view of the surgical fastening apparatus employing an alternative embodiment of the adjustable closure mechanism of the present invention.

Referring now in specific detail to the drawings, in which like reference numerals identify similar or identical elements throughout the several views, FIG. 1 shows a surgical fastening instrument 10 which employs the adjustable closure mechanism of the present invention. Fastening instrument 10 is provided with a stationary handle 12 and an actuating handle 14 which together comprise the trigger mechanism of instrument 10. An elongated body portion 16 is provided which terminates in a distal jaw mechanism 18 which includes an anvil jaw 20 and a cartridge jaw 22. A fastening cartridge (not shown) is positioned within cartridge jaw 22 for driving staples or fasteners through tissue against an anvil surface positioned on anvil jaw 20. Alternatively, the cartridge can contain the fastener portions of two part fasteners which are driven into retainers positioned on a carrier 21 on the anvil jaw as seen in FIG. 10. At the handle end of instrument 10 is provided a push button 26 for operating an advancement preparation mechanism 28, whose function will be described below.

Figure 2:
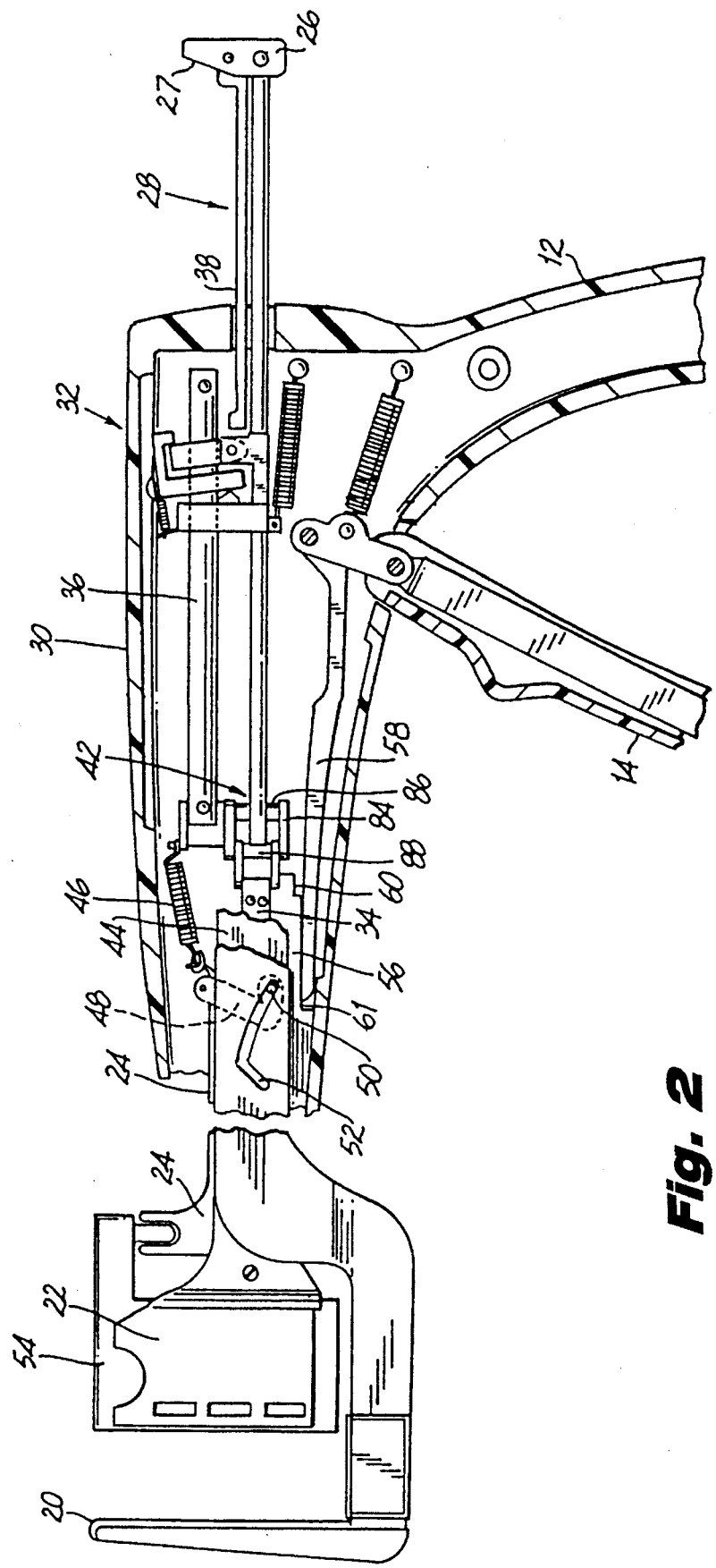
FIG. 2 illustrates a side cross-sectional plan view of a surgical fastening instrument employing the adjustable closure mechanism of the present invention in which the instrument is in an at rest condition.

As seen in FIG. 2, push button 26 and advancing mechanism 28 extend outwardly from the handle end of the instrument 10. A releasable retaining mechanism 32 is slidably engaged to the stationary rod member 36 and is coupled to slider mechanism 40 so that as slider mechanism 40 is urged forwardly into housing 30, retaining mechanism 32 is slidably retained along stationary rod member 36 rod member 38, such that release rod member 38 and slider mechanism.

Advancing mechanism 28 comprises slider mechanism 40 including an elongated member. A release rod member 38 and the slider mechanism 40 are secured to push button 26. Thrusting push button 26 towards housing 30 slides release rod 38 and slider mechanism 40 into the housing to move the retaining mechanism 32 along rod 36. Slider mechanism 40 extends to linkage structure 42 to activate the linkage structure 42 and urge jaw mechanism 18 distally. Linkage structure 42 moves movable rod 34, as well as fastener driver 56, cartridge frame 44, alignment pin advancement means 24, and cartridge 54 all in a distal direction to selectively position movable cartridge jaw 22 and stationary anvil jaw 20.

For purposes of clarity, the individual mechanisms will be described separately, and then the overall operation of the device will be discussed.

Figure 7A:
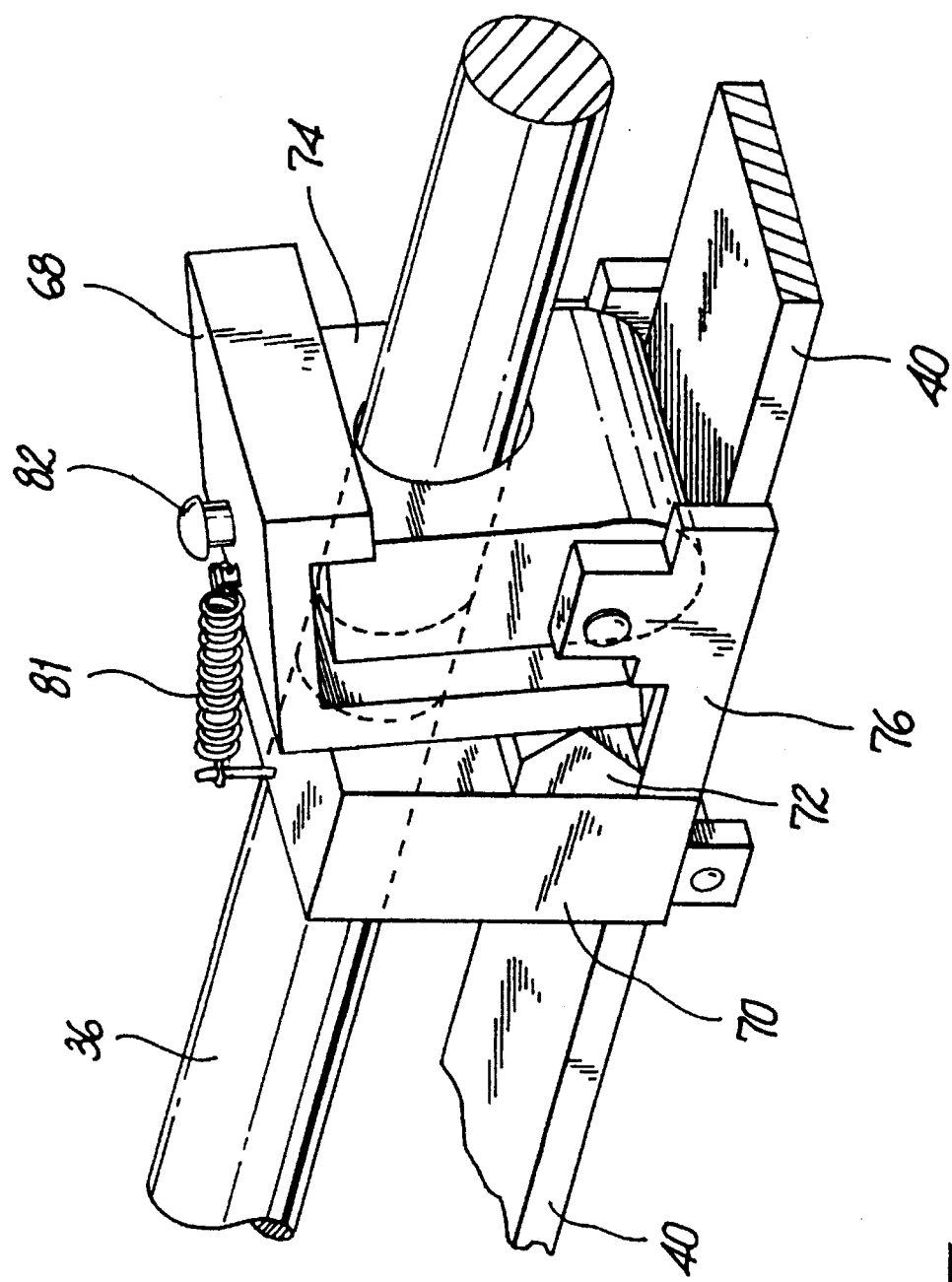
FIG. 7A illustrates a perspective view of the retaining means of the device of FIG. 7.
Figure 15B:
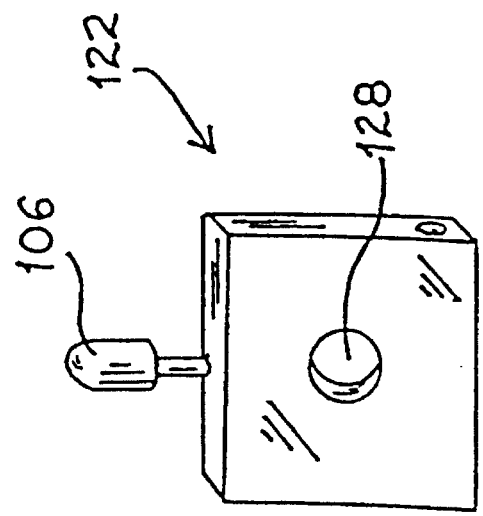
FIGS. 15A and 15B illustrate embodiments of the retaining means of the adjustable closure mechanism of the present invention.
Figure 15A:
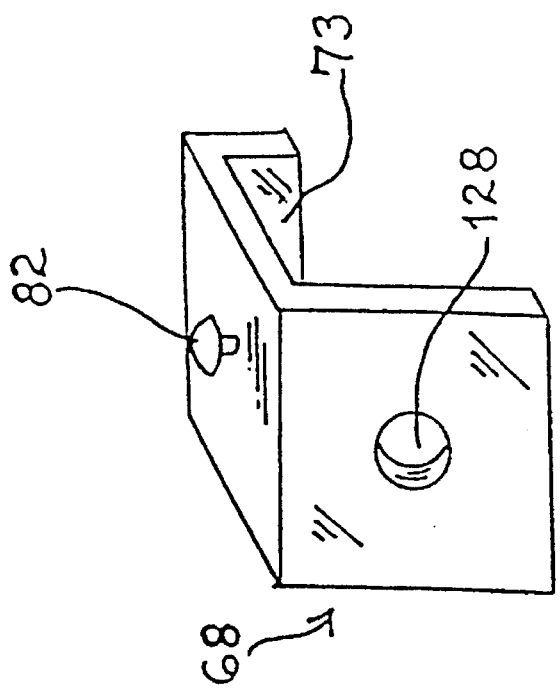

FIG. 7 illustrates a retaining mechanism of the present invention, which slidably engages the stationary rod 36, and which acts in conjunction with the linkage structure 42 to selectively position the jaw mechanism 18 of the surgical fastener apparatus 10. Retaining mechanism 32 is coupled to slider mechanism 40 and is urged rearwardly by biasing spring 80 as shown. The retaining mechanism 32 comprises a clamp member 68, a block member 70, and a spring member 81. The clamp member is provided with a central bore 128 through which stationary rod 36 passes. Clamp member 68 is best seen in FIG. 15A. The clamp member 68 is pivotally secured to the block member 70 and biased into a locking engagement of stationary rod 36 by the spring member 81. Spring member 81 may comprise a coiled spring as shown, or may further comprise any other biasing mechanism such as a leaf spring, rubber block, or the like. Block member 70 may be provided with a central bore (not shown) through which stationary rod 36 passes, or alternatively, block member 70 may have a substantially U-shaped portion to allow stationary rod 36 to pass therethrough. Block member 70 further comprises shoulder portion 72 which abuts the lower portion of clamp member 68 as shown to provide a pivot point for releasing clamp member 68, as will be described below. Block member 70 is slidably secured on rod 36 within body portion 16.

As best seen in FIG. 15A, clamp member 68 has an L-shaped portion terminating in a contact face 73 which engages a release mechanism comprising a release lever 74 and a release rod 38. The release lever 74 is pivotably connected to carriage 76 and pivots about pivot point 79. Release lever 74 preferably has a central bore to allow a stationary rod 36 to pass therethrough, but may also be provided with a U-shaped body both to surround stationary rod 36 and engage contact face 73 of clamp member 68. Clamp member 68 is further provided with a guide post 82 which slides within a guide track 83 to fully align clamp member 68 in relation to stationary rod 36.

Figure 6:
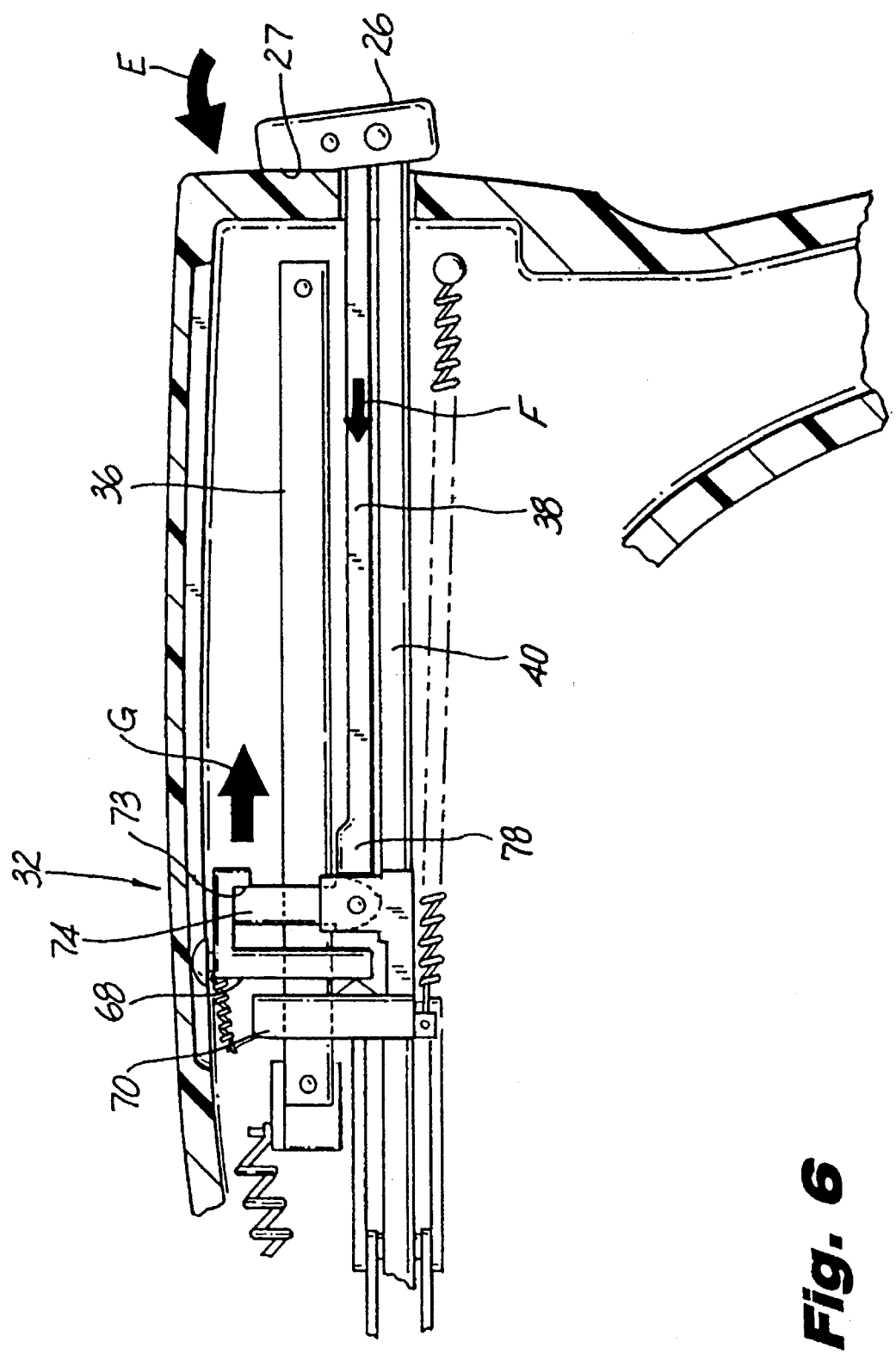
FIG. 6 illustrates a partial enlarged view of the handle end of the device of FIG. 2 showing the release mechanism for disengaging the retaining means of the present invention.

As shown in FIG. 7, clamp member 68 is biased at an angle to engage stationary rod 36 so that edges of central bore 128 frictionally engage stationary rod member 36. As push button 26 is urged towards housing 30, retaining mechanism 32 slides along stationary rod 36 due to the movement of advancing mechanism 28. Carriage 76 is engaged with movable slider mechanism 40 so that the entire retaining mechanism is urged distally against biasing spring 80. In order to release retaining mechanism 32, as best shown in FIG. 6, push button 26 is rotated in the direction of arrow E until beveled surface 27 contacts housing 30. Pivoting push button 26 in the direction of arrow E moves release rod 38 in the direction of arrow F so that contact surface 78 of release rod 38 pivots release lever 74 to engage contact face 73 of clamp member 68. This pivoting action moves clamp member 68 in the direction of arrow G to release the frictional engagement of the central bore 128 with stationary rod 36. Releasing the frictional engagement causes the entire retaining mechanism 32 to return in the direction of arrow G to the position shown in FIG. 7. This movement is caused by biasing spring 80 (not shown in FIG. 6) which moves the entire mechanism to the position shown in FIG. 7.

Figure 8:
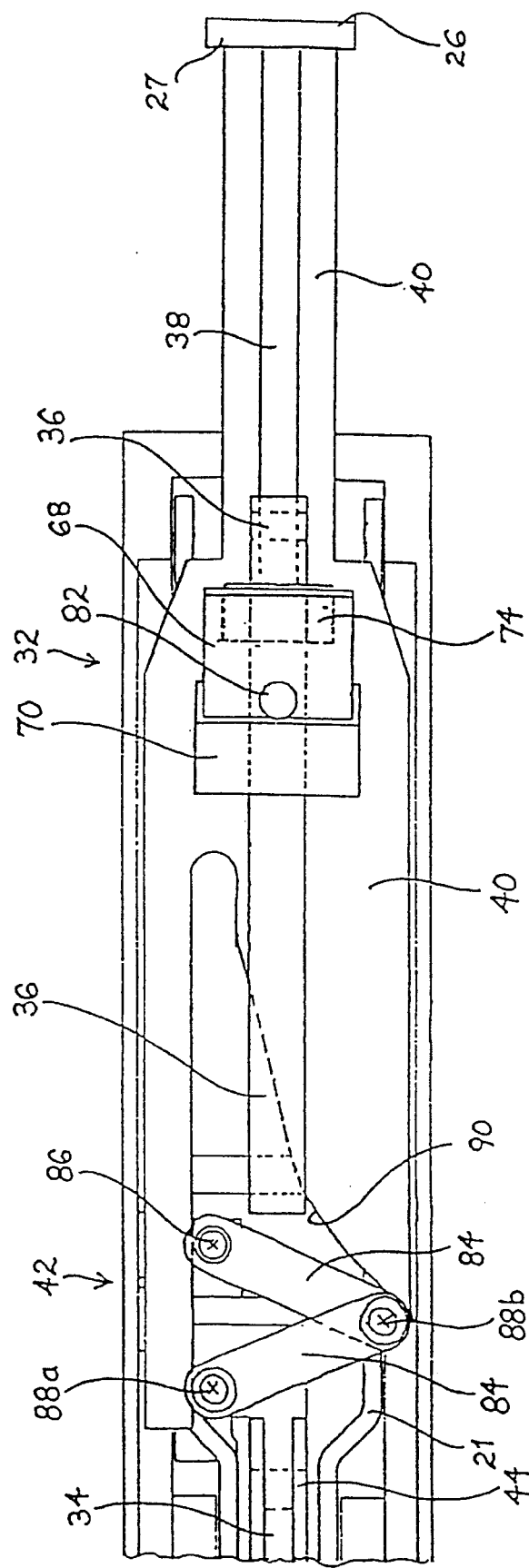
FIG. 8 illustrates a top plan cutaway view of the instrument of FIG. 1 showing the adjustable closure mechanism of the present invention in the at rest condition.
Figure 9:
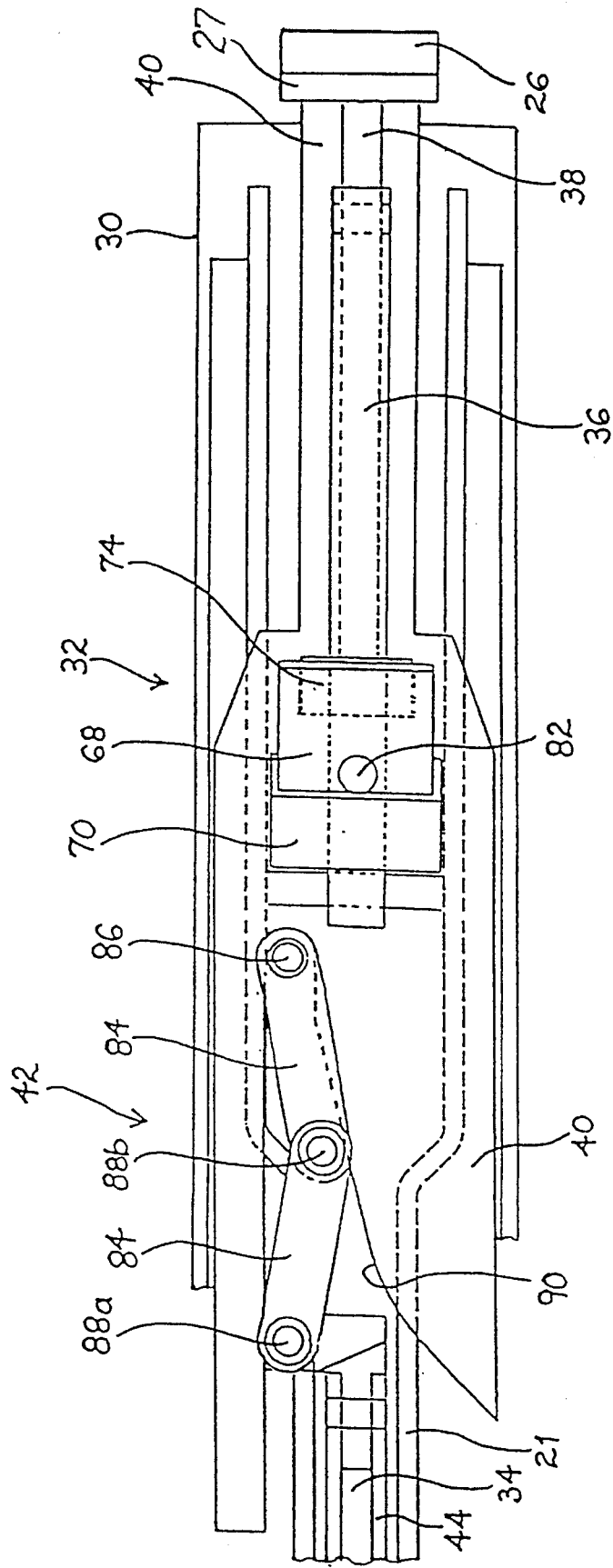
FIG. 9 shows a top plan cutaway view of the instrument of FIG. 1 showing the adjustable closure mechanism of the present invention in the fully deployed condition.

Turning now to FIGS. 8 and 9, there is illustrated the linkage structure 42 and its operation in conjunction with slider mechanism 40 and retaining mechanism 32. Structure 42 comprises a pair of linkage arms 84, which are preferably secured by pivot posts to a second pair of linkage arms 84 located below the pair shown in FIG. 8 in mirror arrangement, as clearly shown in FIGS. 2–6. Linkage arms 84 are joined through stationary pivot post 86, and movable pivot posts 88A and 88B. Movable pivot post 88A is secured to rod 34 and cartridge frame 44 to urge these elements distally when push button 26 is activated. Slider mechanism 40 includes a camming surface 90 which engages movable pivot post 88B to collapse linkage structure 42 to move the rod 34 and cartridge frame 44, and consequently move cartridge jaw 22 towards anvil jaw 20.

As best seen in FIG. 9, as push button 26 is fully actuated to contact housing 30, retaining mechanism 32, being coupled to slider mechanism 40 slides along stationary rod 36. Camming surface 90 engages movable post 88B, driving movable post 88A distally to move movable rod 34 and cartridge frame 44 in relation to housing frame 21 as shown. Releasing retaining mechanism 32 as described above returns linkage structure 42 to the configuration shown in FIG. 8.

It can be appreciated from FIGS. 8 and 9 that the linkage structure 42 provides a two-stage approximation of the jaw mechanism 18, whereby initial movement of the slider mechanism 40 caused a large initial approximation, while a smaller, secondary approximation eases the jaws into approximation at the conclusion of movement of the slider mechanism 40. As slider mechanism 40 is initially moved upon actuation of the push button 26, a large portion of the overall distance cartridge jaw member 22 travels towards anvil jaw member 20 is traversed in the initial movement. Typically, as the slider mechanism 40 travels approximately one-half its overall distance, and correspondingly moving movable pivot post 88A a portion of its total distance, cartridge jaw 22 moves approximately 80% of its total distance. As slider mechanism 40 travels its remaining one-half distance, the cartridge jaw moves its final 20% of its total distance. This allows for a fine adjustment of the jaw mechanism to accommodate the various thickness of tissues positioned between the jaw members.

Instrument 10 employing the novel adjustable closure mechanism of the present invention may further include a coupling device for coupling the fastener driving mechanism to the trigger mechanism only when a proper distance between cartridge jaw 22 and anvil jaw 20 has been reached. This mechanism is best illustrated in FIGS. 14A through 14C.

Figure 3:
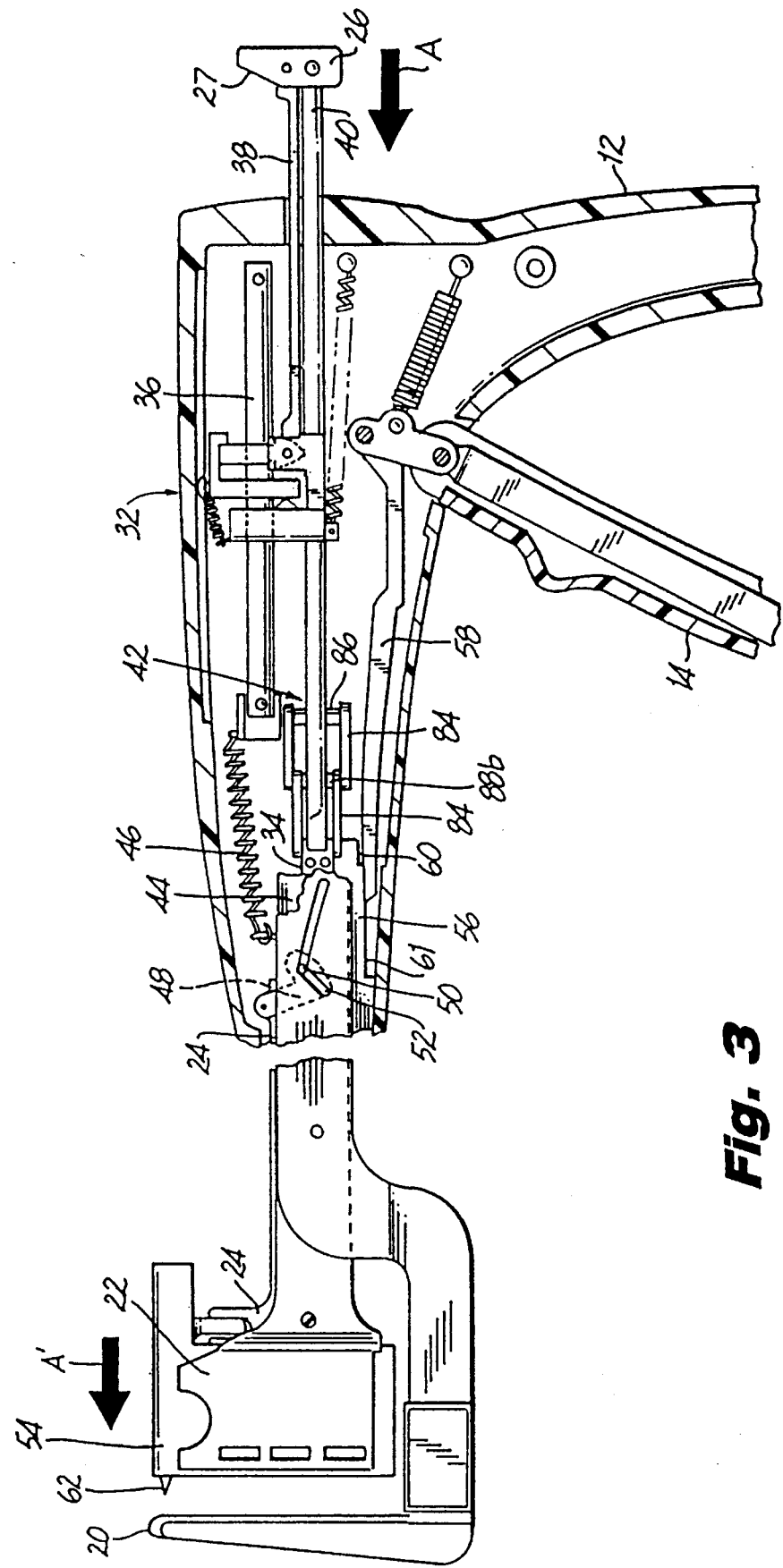
FIG. 3 illustrates the device of FIG. 2 in which the adjustable closure mechanism is activated and the jaw mechanism is partially closed.
Figure 4:
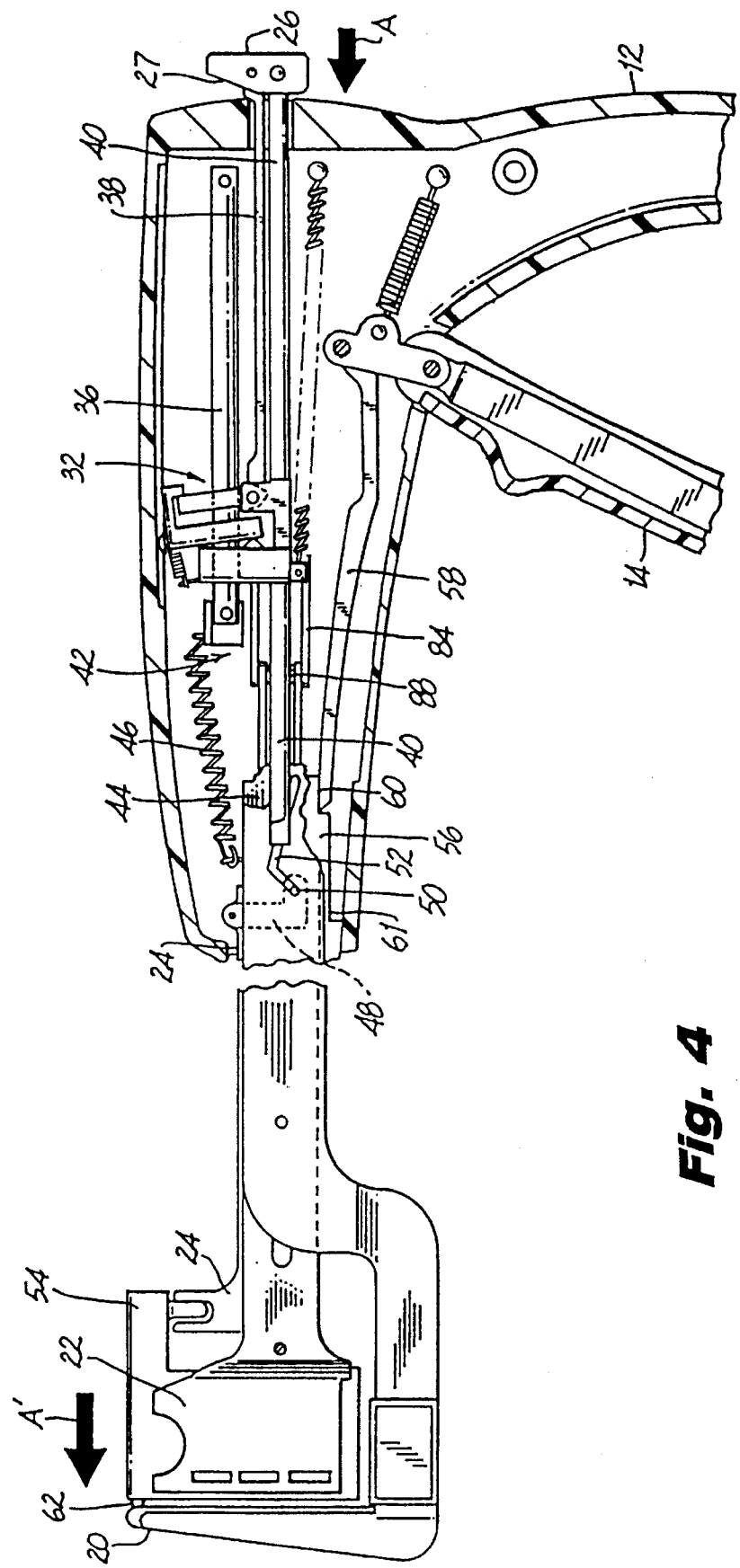
FIG. 4 illustrates the device of FIG. 2 in which the adjustable closure mechanism of the present invention is fully deployed.
Figure 14A:
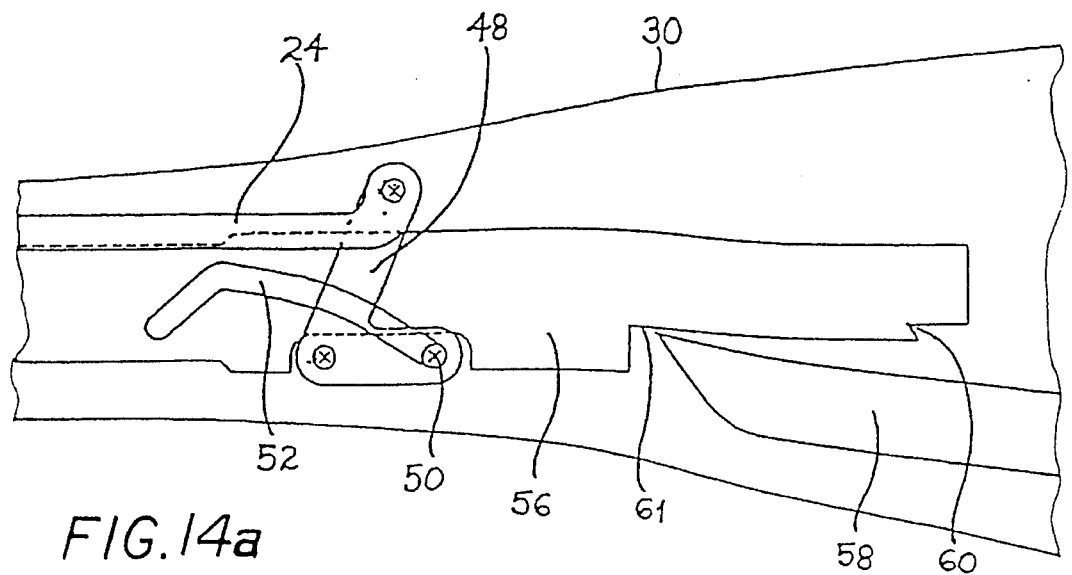
FIGS. 14A–14C illustrate the coupling mechanism according to the present invention for coupling the trigger mechanism to the fastener driving mechanism used in conjunction with the adjustable closure mechanism of the present invention.
Figure 14B:
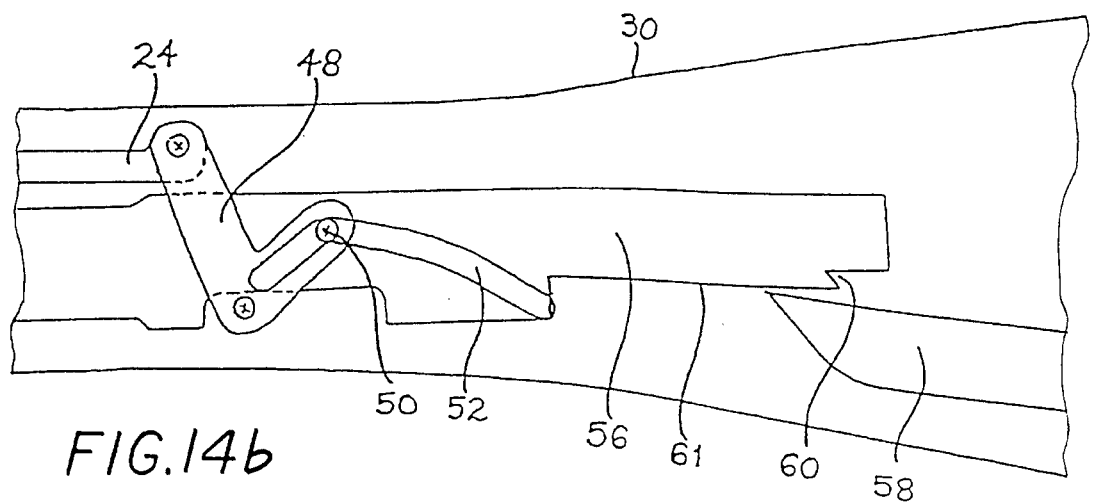
Figure 14C:
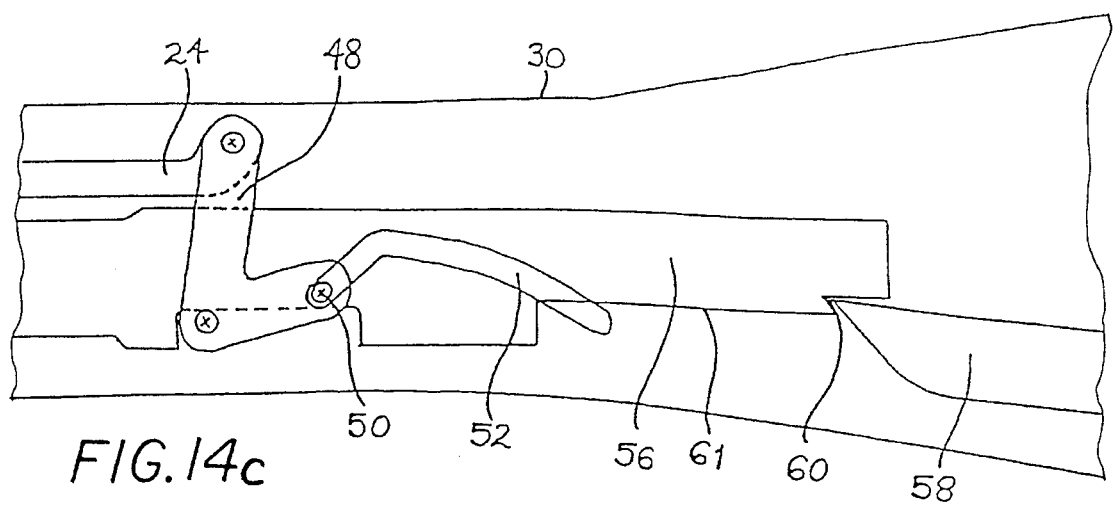

FIGS. 14A through 14C, in conjunction with FIGS. 2–6, illustrate the coupling mechanism of the present invention. Housing frame 21 is provided with a frame track 52 within which a driving pin 50 rides. Driving pin 50 is secured to one leg of an L-shaped driving link 48, where the opposite end of driving link 48 is secured to the alignment pin advancement means 24. Driving link 48 is further coupled to cartridge frame 22 which is advanced distally when push button 26 is actuated so that as link 48 advances as seen in FIGS. 14a–14c, and in FIGS. 2–4, pin advancement means 24 moves distally as seen in FIGS. 2–4 to move pin 62 into engagement with anvil jaw 20. Pin advancement means 24 comprises an arm member which rides on top of driver 56 and terminates in an upturned portion to engage pin 62. As push button 26 is actuated, linkage structure 42 is deployed and fastener driver 56 is moved distally. Prior to actuation of push button 26, fastener driver 56 is in the position shown in FIG. 14A, and coupling arm 58 is positioned on bearing surface 61 as shown. Coupling arm 58 is connected to actuating handle 14 as best seem in FIG. 2. Driver 56 terminates in a fastener drive surface (not shown) which is conventional, and is moved into the position shown in FIG. 14c by the interaction of pin 50 with track 52. Driver 56 is secured to pin 50 and is advanced with pin 50.

As push button 26 is moved, fastener driver 56 is moved forwardly so that coupling arm 58 slides along bearing surface 61 as shown in FIG. 14B. Driving pin 50 travels in frame track 52, while driving link 48 urges alignment pin advancement means 24 as shown. As best seen in FIG. 3, alignment pin advancement means 24 moves forwardly so that alignment pin 62 protrudes from cartridge 54 and aligns with an alignment hole (not shown) in anvil jaw 20. This insures proper alignment of cartridge 54 with anvil jaw 20 so that fastener means 66 are properly driven into position between the jaw members.

As push button 26 is further moved towards housing 30, to the position shown in FIG. 4, cartridge jaw 22 is aligned adjacent anvil jaw 20 so that pin 62 is within the hole in anvil jaw 20. Driving link 48 moves slightly in the proximal direction towards the handle end of instrument 10 to a substantially upright position as shown in FIG. 14C and FIG. 4. This moves alignment pin advancement means 24 slightly proximally to the position shown in FIG. 4 so that alignment pin 62 does not protrude completely through anvil jaw 20.

Figure 5:
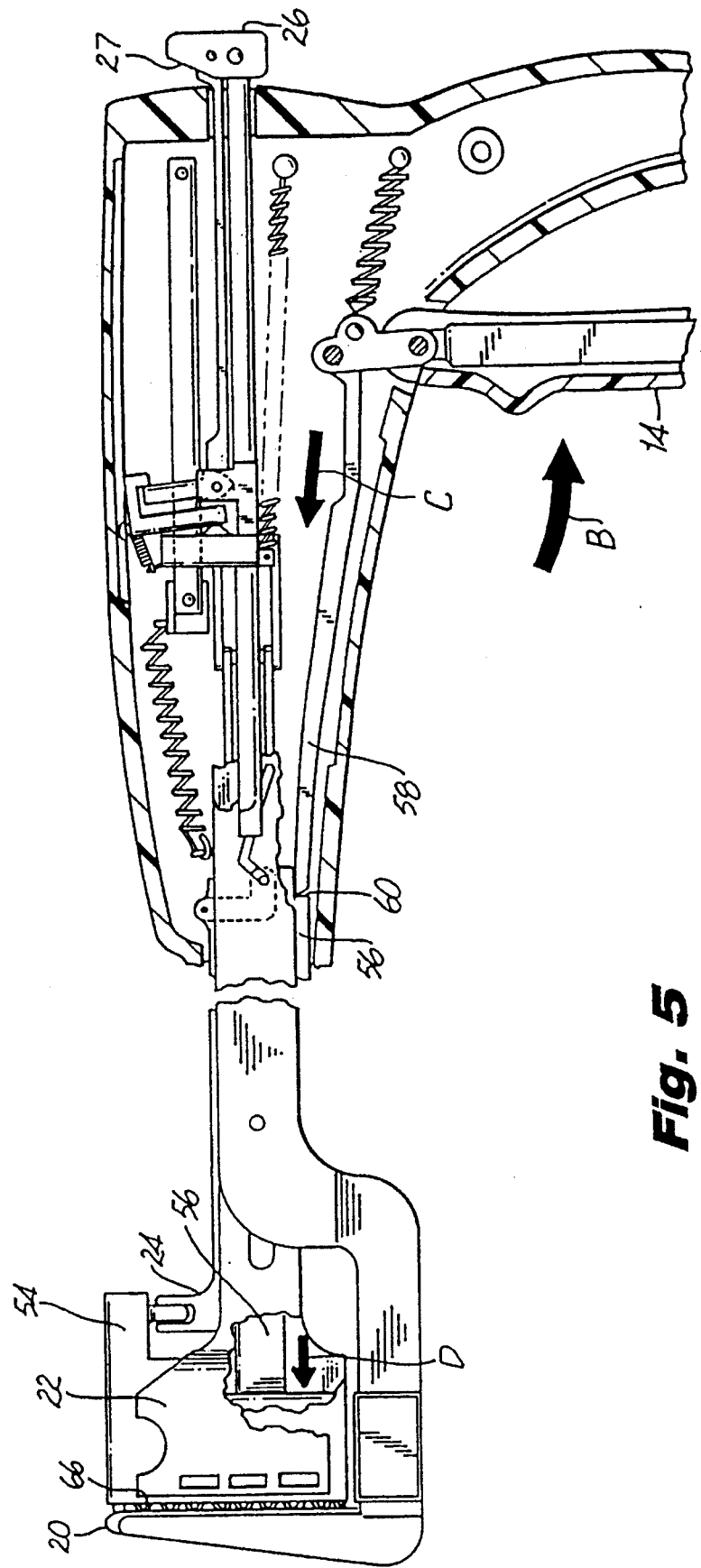
FIG. 5 illustrates the device of FIG. 2 in which the adjustable closure mechanism of the present invention is fully deployed and the trigger mechanism of the device has been actuated so that the fastening means have been driven from the cartridge.

When push button 26 reaches the position shown in FIG. 4, fastener driver 56 has moved distally to a position where coupling arm 58 slides off bearing surface 61 and into notch 60 as shown in FIG. 14C. At this point, driving link 48 has moved to the position shown in FIG. 14C and driving pin 50 has fully traversed the length of frame track 52. In the position shown in FIG. 14C, coupling arm 58 is engaged with fastener driver 56 so that actuation of handle 14 as shown in FIG. 5 will drive fastener means 66 into the tissue as fastener driver 56 moves in the direction of arrow D. Although not shown, coupling arm 58 may be provided with a leaf spring member to urge coupling arm 58 into engagement with notch 60. As push button 26 is rotated to release retaining mechanism 32, driving pin 50 travels proximally in frame track 52, so that when driving pin 50 reaches the position shown in 14B fastener driver 56 is lifted off coupling arm 58 despite the leaf spring, and coupling arm 58 is no longer engaged in notch 60. As retaining means 32 returns the entire mechanism to the position shown in FIG. 2, driving link 48 and fastener driver 56 return to the position shown in FIG. 14A.

Returning now to FIGS. 2 through 6, the operation of the surgical fastener apparatus 10 having the adjustable closure mechanism of the present invention will now be described.

After tissue which is to be surgically repaired is positioned between cartridge jaw 22 and anvil jaw 20, push button 26 is pushed in the direction of arrow A as seen in FIG. 3 which moves slider mechanism 40 and release rod 38 into housing 30. As best seen in FIG. 4, slider mechanism 40 extends to linkage structure 42, so that as retaining mechanism 32 is slid distally along stationary rod 36, camming surface 90 of slider mechanism 40 engages stationary post 88B to deploy linkage structure 42. As linkage structure 42 is deployed, movable rod 34 is urged forwardly along with cartridge frame 44, thus urging driving pin 50 along frame track 52. The force of biasing spring 46 is overcome as push button 26 is urged in the direction of arrow A.

As driving pin 50 moves in track 52, driving link 48 is moved to the position shown in FIG. 3, which urges alignment pin advancement means 24 to the position shown at the jaw mechanism 18. In this position, alignment pin 62 protrudes from cartridge 54 and aligns with the alignment hole in anvil jaw 20 as cartridge 54 moves in the direction of arrow A'.

As linkage structure 42 is deployed and movable rod 34 and cartridge frame 44 move distally, fastener driver 56 also moves distally and coupling arm 58 slides along bearing surface 61.

When push button 26 is fully actuated, linkage structure 42 is fully deployed as shown in FIG. 4, and retaining mechanism 32 frictionally engages stationary rod 36 to maintain instrument 10 in the position shown in FIG. 4. At this time, cartridge 54 has moved into position in the direction of arrow A' so that alignment pin 62 is positioned in the alignment hole in anvil jaw 20. Alignment pin advancement means 24 moves slightly proximally so that alignment pin 62 does not protrude beyond anvil jaw 20, and driving link 48 assumes the position shown in FIG. 4. Driving pin 50 has reached the end of track 52. In the position shown in FIG. 4, actuating arm 58 has slid off bearing surface 61 and into notch 60 of fastener driver 56 so that the device as shown in FIG. 4 is ready to be fired. Once in the position of FIG. 4, actuating handle 14 is moved in the direction of arrow B to fire the fasteners 66. As actuating handle 14 is moved in the direction of arrow B against the force of biasing spring 64, coupling arm 58, having been engaged in notch 60, moves in the direction of arrow C to move fastener driver 56 distally in the direction of arrow D. Fastener driver 56 drives fasteners 66 from cartridge 54 through the tissue (not shown) and into the anvil surface of anvil jaw 20. Upon completion of firing, actuating handle 14 is released and returns to the position shown in FIG. 4.

To remove instrument 10 from the surgical site, it is necessary to release the jaw mechanism 18 to return to the position shown in FIG. 2. This is accomplished by pivoting push button 26 in the direction of arrow E, as best seen in FIG. 6, so that beveled surface 27 contacts the housing 30. As push button 26 is pivoted in the direction of arrow E, release rod 38 travels in the direction of arrow F so that contact surface 78 of release rod 38 pivots release lever 74 as shown, which engages contact face 73 to move clamp member 68 to an upright position and perpendicular in relation to stationary rod 36. This releases the frictional engagement of clamp member 68 with stationary rod 36 and the entire retaining mechanism 32 is moved along stationary rod 36 in the direction of arrow G due to the force of biasing spring 80 (as shown in FIG. 7). The entire mechanism, including the linkage structure 42, jaw mechanism 18, and retaining mechanism 32 is returned to the position shown in FIG. 2.

FIG. 10 illustrates a surgical fastening apparatus 100 employing an alternative adjustable closure mechanism according to the present invention. Apparatus 100 is similar to apparatus 10 of FIG. 1 in that a stationary handle 12 and an actuating handle 14 are provided, along with a body portion 16 and a jaw mechanism 18. Body portion 16 is provided with a flared portion 104 which is symmetrical on both sides of the instrument for accommodating the advancing mechanism which includes movable rod 116, linkage structure 110, and slider mechanism which will be described below. A push button 102 is provided for actuating the slider mechanism, and a release button 106 is provided to release the retaining mechanism as will be described below.

Figure 11:
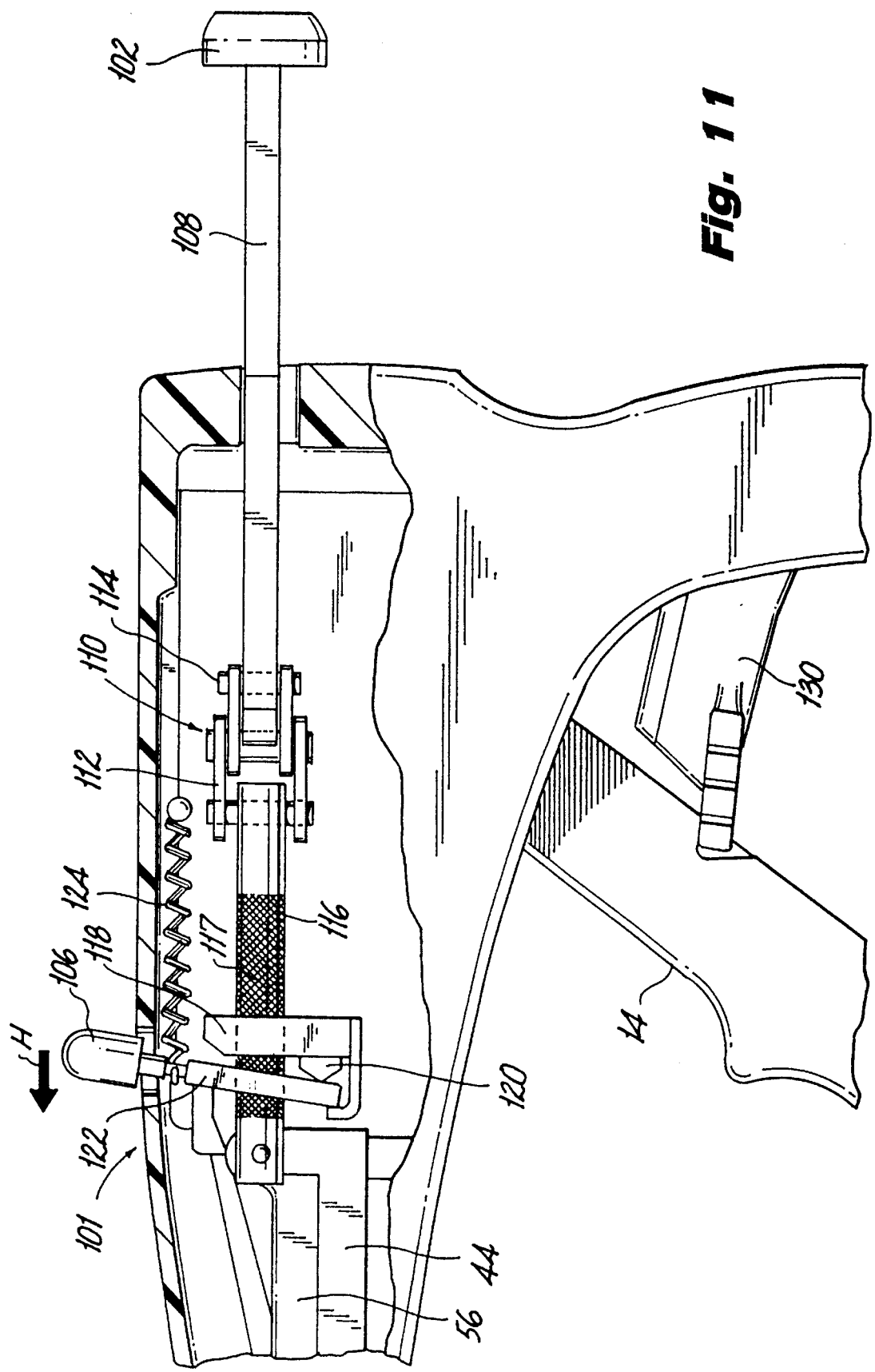
FIG. 11 illustrates a side cutaway view of the handle end of the instrument of FIG. 10 showing the adjustable closure mechanism of the present invention.

Turning now to FIG. 11, there is shown the adjustable closure mechanism of the apparatus of FIG. 10. Instrument 100 is substantially identical to instrument 10 except for retaining mechanism 101 and linkage structure 110.

Figure 12:
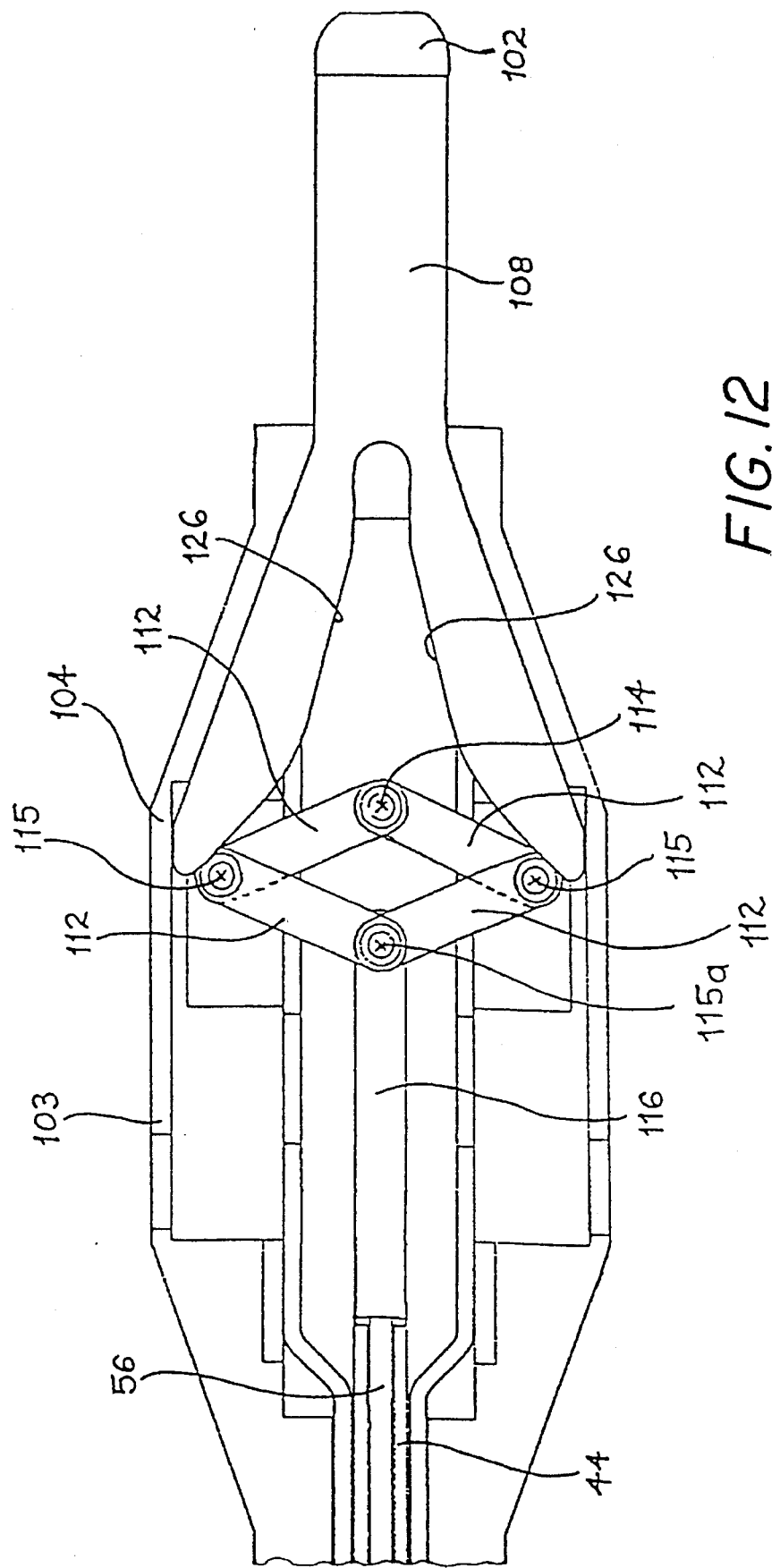
FIG. 12 illustrates a top plan cutaway view of the device of FIG. 10 showing the linkage arrangement of the adjustable closure mechanism of the present invention in an at rest condition.

Linkage structure 110 comprise a plurality of linkage arms 112, as best seen in FIG. 12. Linkage arms 112 form a collapsible box structure having a mirror image as shown in FIG. 11. Linkage arms 112 are joined by stationary pivot post 114 and movable pivot posts 115. As seen in FIG. 12, movable pivot post 115A is secured to movable rod 116 whose function will be described below. Push button 102 is connected to slider mechanism 108 which is provided with an essentially Y-shaped configuration. The outer ends of the Y-shaped slider mechanism are accommodated in flared portions 104 of the housing 103 of instrument 100. Movable rod 116 extends from movable pivot point 115A through retaining mechanism 101 to connect to fastener driver 56 and cartridge frame 44 as shown. Movable rod 116 is frictionally engaged by retaining mechanism 101 to selectively position cartridge jaw 22 in relation to anvil jaw 20.

Retaining mechanism 101 comprises clamp member 122 and block member 118 which is provided with shoulder 120. Clamp member 122, as best seem in FIG. 15B, is provided with a central bore 128 whose edges frictionally engage movable rod 116. Movable rod 116, as well as stationary rod 36 of the embodiment of FIGS. 1–9, may be provided with a scored surface 117 to enhance the frictional gripping of clamp members 122 and 68. Clamp member 122 is biased into the engaged position by biasing spring 124.

In use, push button 102 is urged distally towards housing 103 so that camming surfaces 126 engage movable pivot posts 115. As linkage structure 110 collapses to the position shown in FIG. 13, movable pivot point 115A urges movable rod forwardly through retaining mechanism 101 to move fastener driver 56 and cartridge frame 44 distally to selectively position the jaw mechanism. When push button 102 is in the position shown in FIG. 13, linkage structure 110 is fully collapsed as shown and movable rod 116 is frictionally secured by clamp member 122.

As seen in FIG. 11, a handle locking mechanism 130 may also be provided. To fire the device to drive fasteners through tissue positioned in jaw mechanism 118, locking mechanism 130 is pivoted away from actuating handle 114 and the fasteners are driven through the tissue in the manner described above. To return instrument 100 to the position shown in FIG. 11, a release member comprising a release knob 106 is moved in the direction of arrow H so that clamp member 122 is pivoted about shoulder 120. When clamp member 122 reaches a substantially vertical position perpendicular to movable rod 116, the frictional engagement between the central bore 128 and the movable rod 116 is released, and movable rod 116 returns to the position shown in FIG. 11 due to a biasing spring which is not shown. Release knob 106 is then let go of, and biasing spring 124 returns clamp member 122 to the position shown in FIG. 11.

Linkage structure 110 returns to the position shown in FIG. 12.

As described above in connection with linkage structure 42, movement of linkage structure 110 provides for a two-stage approximation of the jaw mechanism, providing for a large approximation (about 80% of the total distance) of the jaw distance for movement of the first 50% of the slider mechanism 108. The remaining 50% of the movement of the slider mechanism 108 moves the jaw mechanism 18 its remaining 20% of distance, providing for fine adjustment.

The adjustable closure mechanism of the present invention can also be used in other instruments to close the distance between the movable jaw member and stationary jaw member at the stapling or fastening end of the instrument or between two movable jaw members. That is the jaw mechanism may be of the type, wherein one jaw moves toward and away from the other; however, the present invention is also applicable for use with devices of alternative types, i.e., where both jaws move toward and away from each other. The surgical instrument may be of the type which applies metal staples or two part fasteners of the bioabsorbable type.

The surgical stapling or fastening instrument employing the adjustable closure mechanism of the present invention is a device which may be operated with one hand to effect the closure motion of the jaw members of the instrument followed by activation of the trigger mechanism to fire the staples or fasteners into the tissue. The complex rotational or pivoting arrangement of the prior art devices is eliminated, resulting in a lightweight and easy to handle instrument which is inexpensive to manufacture and easy to assemble.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for applying surgical fasteners to body tissue comprising:

tissue gripping means for holding tissue therebetween including a first jaw member and a second jaw member, said first jaw member including a plurality of fasteners positioned on said first jaw member;

means for advancing said first jaw member towards said second jaw member to grip tissue therebetween prior to driving said fasteners into said tissue;

means for retaining said advancing means along a linear path of travel to selectively position said first jaw member in a plurality of positions in relation to said second jaw member;

means for releasing said retaining means from engagement with said advancing means, said releasing means being movable from a first position which permits said retaining means to engage said advancing means to a second position in which said releasing means engages said retaining means to move said retaining means out of engagement with said advancing means to permit said advancing means to return to a rest position; and means for driving said fasteners into said tissue subsequent to positioning said jaw members in relation to each other by said advancing means.

2. An apparatus according to claim 1, further comprising means for actuating said driving means to drive said fasteners into said tissue.

3. An apparatus according to claim 2, further comprising means for coupling said driving means to said actuating means, said driving means driving said fasteners only when said first jaw member is approximated a predetermined distance towards said second jaw member.

4. An apparatus according to claim 3, wherein said coupling means comprises a bearing surface on said driving means for engaging an arm member of said actuating means for driving said fasteners only when said first jaw member is approximated to said predetermined distance towards said second jaw member.

5. An apparatus according to claim 4, wherein said bearing surface comprises a notch for engaging said arm member.

6. An apparatus according to claim 2, wherein said advancing means is coupled to said driving means to advance said driving means into a firing position.

7. An apparatus according to claim 6, further comprising means for coupling said driving means to said actuating means, said driving means driving said fasteners when said driving means is advanced to said firing position.

8. An apparatus according to claim 7, wherein said coupling means comprises a notch in said driving means for engaging an arm member of said actuating means when said driving means is advanced to said firing position.

9. An apparatus according to claim 1, wherein said advancing means is linearly slidable.

10. An apparatus according to claim 1, further comprising cartridge means for accommodating said plurality of fasteners, said cartridge means being releasably secured to said first jaw member.

11. An apparatus according to claim 10, further comprising means associated with said advancing means for guiding and aligning said cartridge means with said second jaw member.

12. An apparatus according to claim 11, wherein said guide means comprises a slide bar secured at a proximal end through a linking arrangement to said advancing means, and at a distal end to a guide pin which passes through said cartridge means and said second jaw member to align said cartridge means and said second jaw member.

13. An apparatus according to claim 12, wherein said linking arrangement comprises at least one "L" shaped member pivotably secured to said advancing means through a pivot pin, said pivot pin slidably mounted in an arcuate track in a frame member of said apparatus.

14. An apparatus according to claim 12, wherein said advancing means advances said first jaw member towards said second jaw member an initial distance followed by a secondary distance, said initial distance being greater than said secondary distance.

15. An apparatus according to claim 14, wherein said initial distance is approximately four times greater than said secondary distance, said advancing means advancing 50% of its full distance for said initial distance of said jaw member and 50% of its full distance for said secondary distance of said jaw member.

16. An apparatus according to claim 1, wherein said second jaw member includes an anvil surface for bearing against said fasteners.

17. An apparatus according to claim 1, wherein said second jaw member includes means for holding a plurality of retainers, said retainers having means for receiving said fasteners.

18. An apparatus according to claim 1, wherein said release means comprises a pivotable knob to disengage said retaining means.

19. An apparatus according to claim 1, wherein said advancing means comprises a movable rod extending distally through a housing of said apparatus and being thumb-actuable by an operator to advance said first jaw member.

20. An apparatus according to claim 19, wherein said movable rod is scored to provide an enhanced gripping surface for said retaining means to retain said rod movable.

21. An apparatus according to claim 19, wherein said movable rod terminates within said housing in a linkage structure, said linkage structure comprises a plurality of pivoting arm members, said linkage structure being collapsible from a first position to a second position during advancement of said advancing means to advance said first jaw member towards said second jaw member.

22. An apparatus according to claim 21, wherein said arm members pivot about post members to collapse said structure from said first position to said second position, and said arm members being further pivotable to return said structure from said second position to said first position during reciprocable movement of said advancing means.

23. An apparatus according to claim 21, wherein said linkage structure comprises at least two arm members joined by pivoting post members.

24. An apparatus according to claim 23, wherein said linkage structure comprises at least two pairs of arm members, said pairs of arm members spaced from each other and being joined by said post members.

25. An apparatus according to claim 23, further comprising a linkage slider mechanism having at least one camming surface for engaging said post members to collapse said linkage structure, said slider mechanism extending beyond said housing of said apparatus and terminating in a push button member.

26. An apparatus according to claim 21, wherein said linkage structure comprises at least four arm members arranged in a substantially square shape in said first position, said arms being joined by pivoting post members.

27. An apparatus according to claim 26, wherein said linkage structure comprises at least two pairs of four-arm square structures spaced from each other and being joined by said post members.

28. An apparatus according to claim 26, further comprising a linkage slider mechanism having at least one camming surface for engaging said post members to collapse said linkage structure, said slider mechanism extending beyond said housing of said apparatus and terminating in a push button member.

29. An apparatus according to claim 28, wherein said linkage slider mechanism has a generally "Y" shape forming a pair of camming surfaces.

30. An apparatus according to claim 21, further comprising a linkage slider mechanism for collapsing said linkage structure to advance said movable rod to urge said first jaw member towards said second jaw member, said slider mechanism extending beyond said housing of said apparatus and terminating in a push button member.

31. An apparatus according to claim 30, wherein said slider mechanism comprises at least one camming surface for engaging said linkage structure.

32. An apparatus according to claim 30, wherein said retaining means is coupled to said slider mechanism and said advancing means, such that said retaining means moves within said housing upon movement of said slider mechanism, said slider mechanism being example to said means for releasing said retaining means to return said apparatus to a rest position.

33. An apparatus according to claim 32, wherein said releasing means comprises a release rod coupled to said push button member, said push button member being pivotable to advance said release rod to contact and disengage said retaining means to return said apparatus to said rest position.

34. An apparatus according to claim 33, wherein said retaining means comprises a pivotable clamp member.

35. An apparatus according to claim 32, wherein said advancing means further comprises a stationary guide rod, said retaining means being slidingly secured to said stationary guide rod, such that said retaining means moves along and releasably retains said guide rod to selectively position said advancing means and said jaw members.

36. An apparatus according to claim 32, wherein said retaining means comprises a pivotable clamp member having a central bore through which said advancing means passes, an edge of said central bore engaging said advancing means to retain said advancing means and selectively position said first jaw member in relation to said second jaw member.

37. An apparatus according to claim 21, wherein said retaining means comprises a pivotable clamp member having a central bore through which said advancing means passes, an edge of said central bore engaging said advancing means to retain said advancing means and selectively position said first jaw member in relation to said second jaw member.

38. An apparatus according to claim 19, wherein said retaining means comprises a pivotable clamp member having a central bore through which said advancing means passes, an edge of said central bore engaging said advancing means to retain said advancing means and selectively position said first jaw member in relation to said second jaw member.

39. An apparatus according to claim 38, wherein said advancing means further comprises a stationary guide rod, said guide rod passing through said central bore such that said clamp member slidingly advances along said guide rod to selectively position said advancing means and said guide members.

40. An apparatus according to claim 1, wherein said retaining means comprises a pivotable clamp member having a central bore through which said advancing means passes, an edge of said central bore engaging said advancing means to retain said advancing means and selectively position said first jaw member in relation to said second jaw member.

41. An apparatus according to claim 40, wherein said clamp member is biased to an engaged position such that said clamp member is at an angle to said advancing means.

42. An apparatus according to claim 41, further comprising release means for disengaging said clamp member from said advancing means.

43. An apparatus according to claim 40, wherein said advancing means comprises a movable rod.

44. An apparatus for applying surgical fasteners to body tissue comprising:

tissue gripping means for holding tissue therebetween including a pair of jaw members, one of said jaw members including a plurality of fasteners;

means for advancing at least one of said jaw members towards another of said jaw members to grip tissue therebetween prior to driving said fasteners into said tissue, said advancing means including a push knob at a proximal end of the apparatus for advancing a slidable rod member operatively connected to said at least one of said jaw members;

means for retaining said advancing means along a linear path of travel to selectively position said at least one jaw member in relation to said other jaw member;

means for releasing said retaining means from engagement with said advancing means, said releasing means being operable to disengage said retaining means from said advancing means to permit said advancing means to return to a rest position; and a handle mechanism operatively connected to a means for driving said fasteners into said tissue subsequent to positioning said jaw members in relation to each other by said advancing means.

45. An apparatus for applying surgical fasteners to body tissue comprising:

tissue gripping means for holding tissue therebetween including a pair of jaw members, one of said jaw members including a plurality of fasteners;

a first advancing mechanism for manually advancing at least one of said jaw members towards another of said jaw members to grip tissue therebetween prior to driving said fasteners into said tissue;

means for retaining said first advancing means along a linear path of travel to selectively position said at least one jaw member in relation to said other jaw member, said retaining means being mounted for pivoting movement from an engaged position to a disengaged position;

means for releasing said retaining means from engagement with said first advancing means, said releasing means being mounted for sliding movement in relation to said retaining means to pivot said retaining means between said engaged and disengaged positions to permit said first advancing means to return to a rest position;

means for driving said fasteners into said tissue subsequent to positioning said jaw members in relation to each other by said advancing means; and an actuating mechanism for manually advancing said driving means to drive said fasteners into said tissue;

wherein said first advancing mechanism is operable in response to a first movement, and said actuating mechanism is operable in response to a second movement, said first movement being independent of said second movement.

46. An apparatus for applying surgical fasteners to body tissue comprising:

a handle mechanism having at least one movable handle member;

first and second jaw members, said first jaw member having a plurality of fasteners positioned thereon and being movable in relation to said second jaw member;

a pusher mechanism disposed adjacent said handle mechanism for advancing said first jaw member towards said second jaw member to position tissue therebetween prior to driving fasteners into the tissue;

a clamp member for releasably engaging said pusher mechanism to selectively position said first jaw member in relation to said second jaw member;

a release member associated with said clamp member to disengage said clamp member from said pusher mechanism to return said first jaw member to a rest position; and a drive bar associated with said handle mechanism at a first end and said first jaw member at a second end, said drive bar being movable in response to movement of said movable handle member to drive said fasteners into tissue.

47. An apparatus according to claim 46, wherein said pusher mechanism includes a movable rod, said movable rod being frictionally engaged by said clamp member to position said jaw members in relation to each other.

48. An apparatus according to claim 47, wherein said release member and said movable rod are secured to a common push knob and movable in tandem to advance said first jaw member towards said second jaw member, said push knob being pivotable to further advance said release member to contact said clamp member to release said pusher mechanism.

49. An apparatus according to claim 47, wherein said clamp member includes an opening through which said movable rod passes, said clamp member being movable between a first position in which said opening is substantially coaxial with said movable rod so as to allow said pusher mechanism to move freely, and a second position in which said opening is substantially eccentric with respect to a longitudinal axis of said movable rod to frictionally engage said movable rod to position said jaw members in relation to each other.

50. An apparatus for applying surgical fasteners to body tissue comprising:

a first jaw member having a plurality of fasteners;

a second jaw member disposed in opposing relation to said first jaw member;

a pusher mechanism for advancing said first jaw member towards said second jaw member to grip tissue therebetween prior to driving said fasteners into the tissue;

a clamp member for releasably engaging said pusher mechanism along a linear path of travel to selectively position said first jaw member in relation to said second jaw member;

a release member coupled to said pusher mechanism, said release member being operable to selectively contact the clamp member to disengage the clamp member with the pusher mechanism to return the pusher mechanism to a rest position;

a handle mechanism having at least one movable handle member; and a driving rod member operatively associated with and movable in response to movement of said handle mechanism, said driving rod member terminating at said first jaw member to drive said fasteners into tissue upon movement of said handle mechanism.

51. An apparatus for applying surgical fasteners to body tissue comprising:

a first jaw member having a plurality of fasteners;

a second jaw member disposed in opposing relation to said first jaw member;

an advancing mechanism for advancing said first jaw member towards said second jaw member to grip tissue therebetween prior to driving fasteners into the tissue;

a retaining mechanism for retaining the advancing mechanism to permit the advancing mechanism to selectively position the first jaw member in relation to the second jaw member, the retaining mechanism being mounted for movement between a first position to retain the advancing mechanism and a second position to release the advancing mechanism;

a release mechanism being mounted for movement with respect to the retaining mechanism such that movement of the release mechanism effects movement of the retaining mechanism between the first and second positions; and a firing mechanism for driving said fasteners into tissue subsequent to positioning of said first jaw member in relation to said second jaw member by said advancing mechanism.

52. An apparatus according to claim 51, wherein the release mechanism is mounted for longitudinal sliding movement.

53. An apparatus according to claim 52, wherein the retaining mechanism has an opening to receive the advancing mechanism.

54. An apparatus according to claim 53, wherein the retaining mechanism is mounted for pivoting movement with respect to the advancing mechanism.

55. An apparatus according to claim 53, wherein said advancing mechanism includes a push knob and a slidable rod member, said rod member passing through said opening in said retaining mechanism.

56. An apparatus according to claim 55, further comprising a handle mechanism operatively associated with said firing mechanism to drive said fasteners into tissue.

57. An apparatus according to claim 56, wherein said firing mechanism further includes a drive rod member coupled to said first jaw member, such that movement of said drive rod member drives said plurality of fasteners from said first jaw member.

58. An apparatus for applying surgical fasteners to body tissue comprising:

a housing;

a handle having a movable handle member;

first and second jaw members, the first jaw member having a plurality of fasteners positioned thereon and being movable in relation to the second jaw member;

a pusher mechanism extending within the housing and being movable therein, the pusher mechanism operably connected to the first jaw member, wherein the pusher mechanism is movable to advance the first jaw member towards the second jaw member;

a stationary member supported within the housing;

a clamp member operably associated with the pusher mechanism and movable to releasably engage the stationary member to selectively position the first jaw member in relation to the second jaw member;

a release member associated with the clamp member and movable to disengage the clamp member from the stationary member to permit the first jaw member to return to a rest position; and a drive member operably associated with the handle member at a first end and the first jaw at a second end, the drive member being movable in response to movement of the handle member to drive the fasteners into tissue.

59. An apparatus according to claim 58 wherein the pusher mechanism includes a slidable rod, the clamp member being pivotably connected to the slidable rod such that the clamp member can be pivoted from a position engaging the stationary member to a disengaged position.

60. An apparatus according to claim 58 wherein the clamp member includes an opening through which the stationary member passes, the clamp member being movable between a first position in which the opening is substantially coaxial with the stationary member so as to allow the pusher mechanism to move freely, and a second position in which the opening is substantially eccentric with respect to the stationary member to frictionally engage the stationary member to position the jaws in relation to each other.

61. An apparatus according to claim 60 further including a biasing member to bias the clamp member to the second position.

62. An apparatus according to claim 58 wherein the pusher mechanism includes a an elongated member, the release member and the elongated member being secured to a common push knob and movable in tandem to advance the first jaw member towards the second jaw member, the push knob being pivotable to further advance the release member to contact the clamp member to permit the jaw member to return to the rest position.

63. An apparatus for applying surgical fasteners to body tissue comprising:

a housing;

a handle having a movable handle member;

first and second jaw members, the first jaw member having a plurality of fasteners positioned thereon and being movable in relation to the second jaw member;

a pusher mechanism extending within the housing and being movable therein, the pusher mechanism operably connected to the first jaw member, wherein the pusher mechanism is movable to advance the first jaw member towards the second jaw member;

a clamp member operably associated with the pusher mechanism and movable from an engaged position to selectively position the first jaw member in relation to the second jaw member to a disengaged position to permit the first jaw member to move to a rest position;

a release member operably associated with the clamp member and movable from a first position to a second position to move the clamp member to the disengaged position; and a drive member operably associated with the handle member at a first end and the first jaw at a second end, the drive member being movable in response to movement of the handle member to drive the fasteners into tissue.

64. An apparatus according to claim 63 wherein the pusher mechanism includes a movable rod, the rod being frictionally engaged by the clamp member to position the jaw members in relation to each other.

65. An apparatus according to claim 63 further including a biasing member to bias the clamp member to the engaged position.

66. An apparatus according to claim 64 wherein the clamp member includes an opening through which the movable rod passes, the clamp member being movable between the disengaged position in which the opening is substantially coaxial with the movable rod so as to allow the pusher mechanism to move freely, and the engaged position in which the opening is substantially eccentric with respect to a longitudinal axis of the movable rod to frictionally engage the movable rod to position the jaw members in relation to each other.

* * * * *